(12) United States Patent
Ebata et al.

(10) Patent No.: US 9,164,271 B2
(45) Date of Patent: Oct. 20, 2015

(54) ENDOSCOPE SYSTEM

(75) Inventors: Sadao Ebata, Hachioji (JP); Katsunori Sakiyama, Hokuto (JP)

(73) Assignee: OLYMPUS CORPORATION, Tokyo (JP)

( * ) Notice: Subject to any disclaimer, the term of this patent is extended or adjusted under 35 U.S.C. 154(b) by 606 days.

(21) Appl. No.: 13/432,267

(22) Filed: Mar. 28, 2012

(65) Prior Publication Data

US 2012/0184814 A1 Jul. 19, 2012

Related U.S. Application Data

(63) Continuation of application No. PCT/JP2009/066953, filed on Sep. 29, 2009.

(51) Int. Cl.
*G02B 23/24* (2006.01)
*A61B 1/00* (2006.01)

(52) U.S. Cl.
CPC ........ *G02B 23/2484* (2013.01); *A61B 1/00048* (2013.01); *A61B 1/00105* (2013.01); *A61B 1/00131* (2013.01)

(58) Field of Classification Search
CPC ........... A61B 1/00027; A61B 1/00032; A61B 1/00034; A61B 1/00114; A61B 8/56
USPC ......... 600/109, 136, 138, 139, 160, 110, 112, 600/118
See application file for complete search history.

(56) References Cited

U.S. PATENT DOCUMENTS

| | | | |
|---|---|---|---|
| 7,365,768 B1 | 4/2008 | Ono et al. | |
| 2002/0067408 A1* | 6/2002 | Adair et al. | 348/76 |
| 2002/0184122 A1* | 12/2002 | Yamaguchi et al. | 705/30 |
| 2003/0236446 A1 | 12/2003 | Eino | |
| 2004/0114034 A1* | 6/2004 | Squilla et al. | 348/66 |
| 2005/0010084 A1 | 1/2005 | Tsai | |
| 2005/0171399 A1 | 8/2005 | Rich et al. | |
| 2008/0091065 A1 | 4/2008 | Oshima et al. | |
| 2008/0207996 A1 | 8/2008 | Tsai | |
| 2009/0292167 A1* | 11/2009 | Kimoto | 600/109 |

FOREIGN PATENT DOCUMENTS

| | | |
|---|---|---|
| CN | 1777387 A | 5/2006 |
| JP | 2001-330784 | 11/2001 |
| JP | 2004-032099 | 1/2004 |

(Continued)

OTHER PUBLICATIONS

International Search Report dated Dec. 28, 2009 issued in PCT/JP2009/066953.

(Continued)

*Primary Examiner* — Anhtuan T Nguyen
*Assistant Examiner* — William Chou
(74) *Attorney, Agent, or Firm* — Scully, Scott, Murphy & Presser, PC

(57) ABSTRACT

An endoscope system according to the invention includes a display device including a first connector, plural apparatuses having different functions in which placing sections, on which the display device can be detachably set from a common direction, are respectively provided, and a second connector disposed in common in each of the placing sections and electrically connected to the first connector of the display device to form a pair in a state in which the display device is set on the placing sections.

14 Claims, 32 Drawing Sheets

(56) References Cited

FOREIGN PATENT DOCUMENTS

| | | |
|---|---|---|
| JP | 2005-185358 | 7/2005 |
| JP | 2005-191710 | 7/2005 |
| JP | 2008-086666 | 4/2008 |
| WO | WO 97/15144 A1 | 4/1997 |

OTHER PUBLICATIONS

European Search Report dated Apr. 16, 2013 issued in European Patent Application No. EP 09 85 0030.9.

* cited by examiner

ENDOSCOPE SYSTEM

CROSS REFERENCE TO RELATED APPLICATION

This application is a continuation application of PCT/JP2009/066953 filed on Sep. 29, 2008, the entire contents of which are incorporated herein by this reference.

BACKGROUND OF THE INVENTION

1. Field of the Invention

The present invention relates to an endoscope system including a monitor that displays an image and plural apparatuses to which this monitor is detachably attachable.

2. Description of the Related Art

Traditionally, an industrial endoscope apparatus is inserted into, for example, an inside of an industrial plant or a jet engine to thereby be used for an inspection for checking whether a failure or a deficiency is preset. The industrial endoscope is carried and used in a factory, a repair shop, or the like.

Such conventional industrial endoscope is connected to a monitor, which is a display device, such that a check can be performed on the site during the inspection. For example, Japanese Patent Application Laid-Open Publication No. 2001-330784 discloses a display device of an endoscope that is able to be carried. This display device of the conventional endoscope is a separate device connected to the industrial endoscope using a cable.

SUMMARY OF THE INVENTION

An endoscope system according to the present invention includes: a display device including a first connector, plural apparatuses having different functions in which placing sections, on which the display device can be detachably set from a common direction, are respectively provided; and a second connector disposed in common in each of the placing sections and electrically connected to the first connector of the display device to form a pair in a state in which the display device is set on the placing section.

DETAILED DESCRIPTION OF THE PREFERRED EMBODIMENTS

Embodiments relating to an endoscope system of the present invention are explained below with reference to the drawings.

First Embodiment

First, an endoscope system according to a first embodiment of the present invention is explained. In the following explanation, an endoscope system used for an industrial purpose is explained. However, it goes without saying that the endoscope system is configured to be applicable to an endoscope system used for a medical purpose as well.

Figure 1:
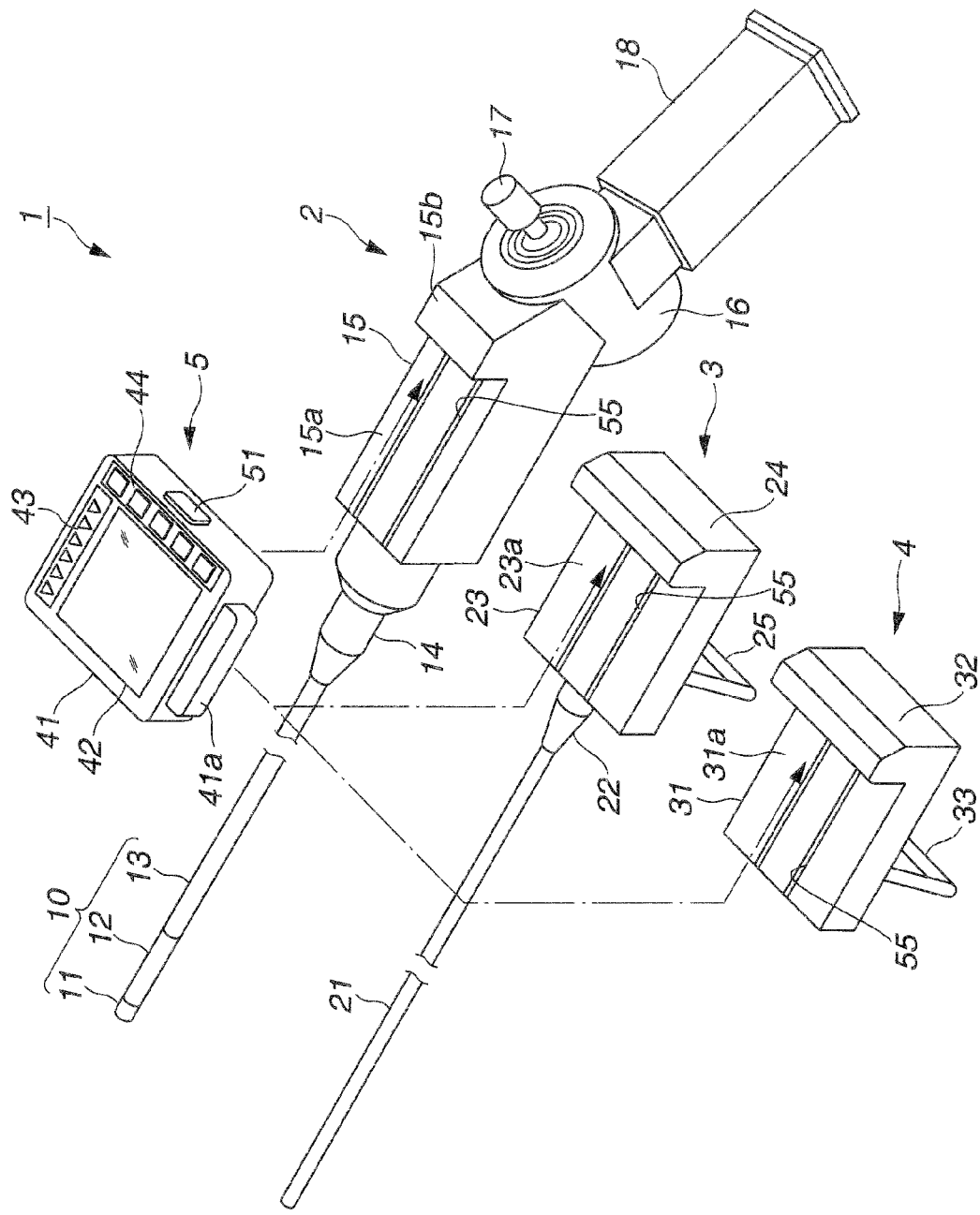
FIG. 1 is a perspective view showing an overall configuration of an endoscope system according to a first embodiment.
Figure 2:
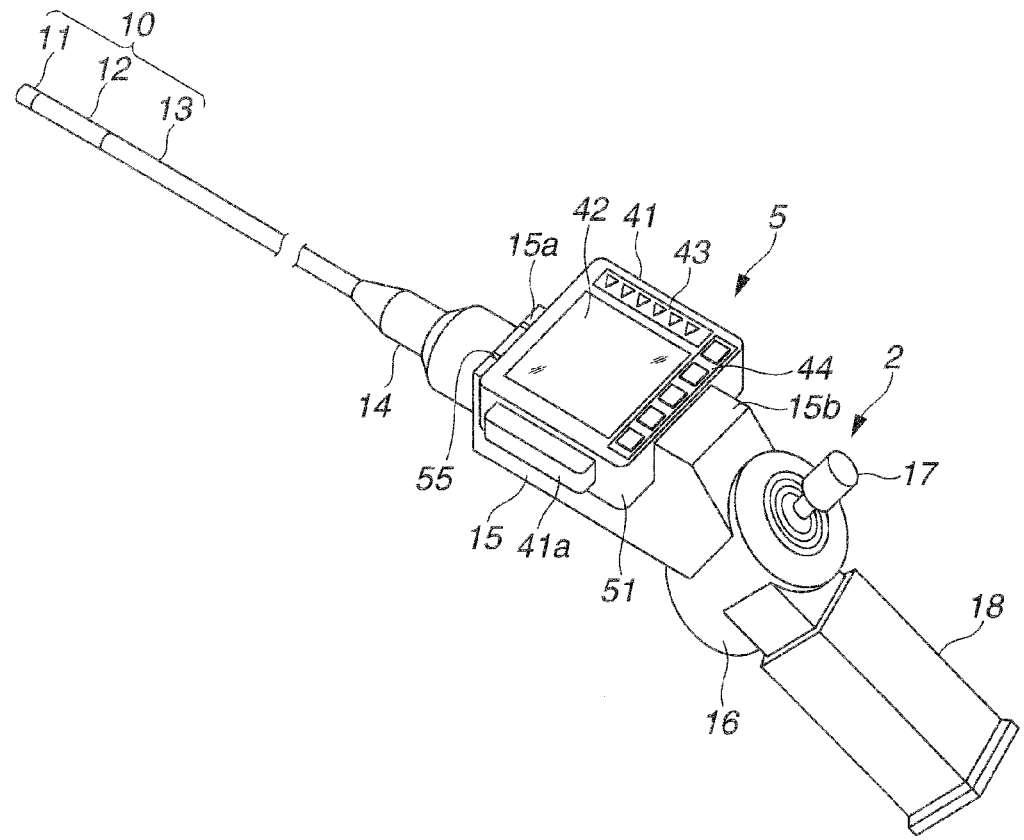
FIG. 2 is a perspective view showing a state in which a display device is placed on a flexible endoscope apparatus according to the first embodiment.
Figure 3:
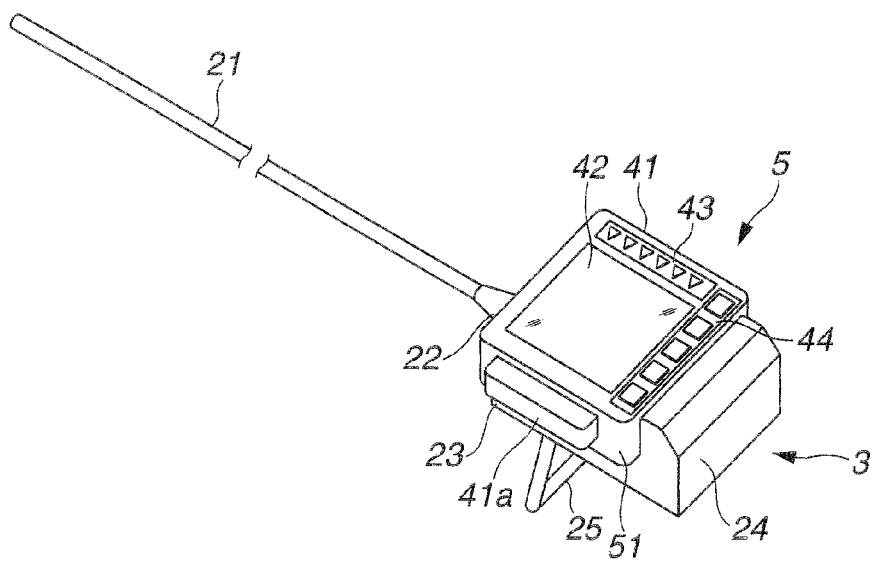
FIG. 3 is a perspective view showing a state in which the display device is placed on a rigid endoscope apparatus according to the first embodiment.
Figure 4:
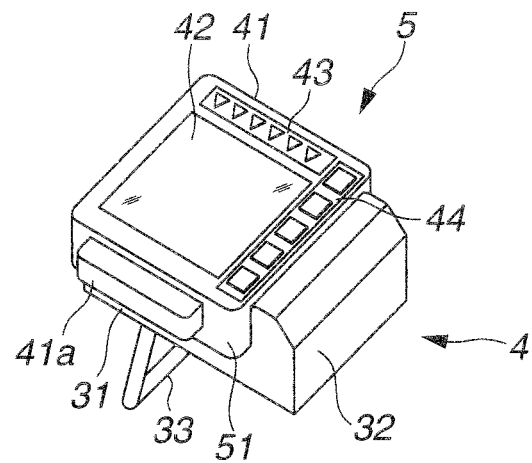
FIG. 4 is a perspective view showing a state in which the display device is placed on a monitor holder according to the first embodiment.
Figure 5:
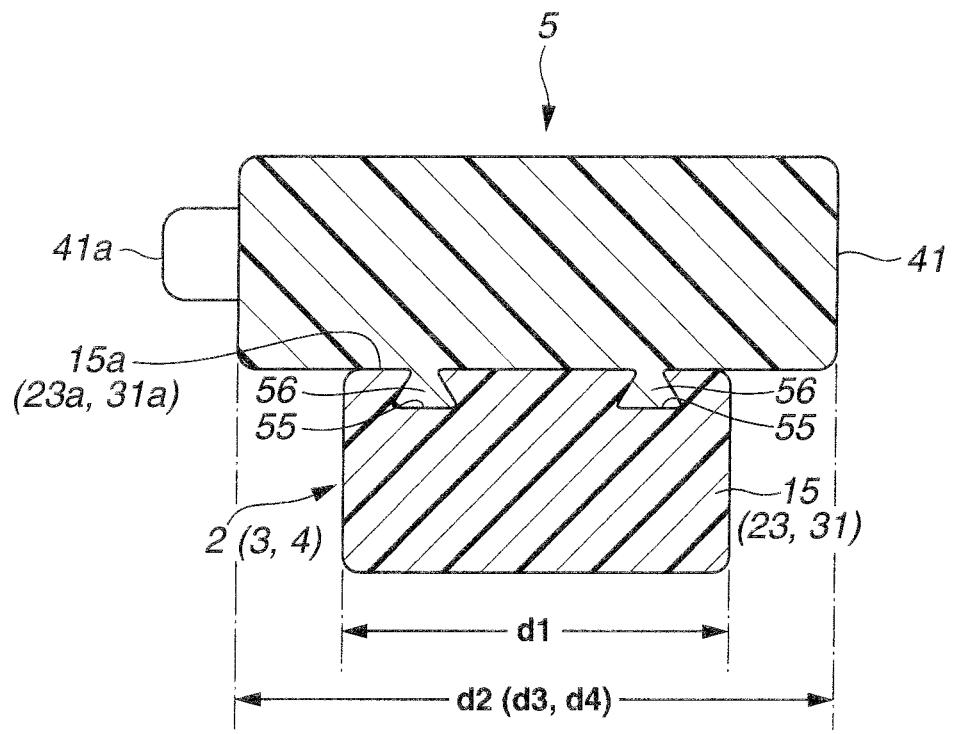
FIG. 5 is a sectional view showing a state in which the display device is placed on the flexible endoscope apparatus, the rigid endoscope apparatus, or the monitor holder according to the first embodiment.
Figure 6:
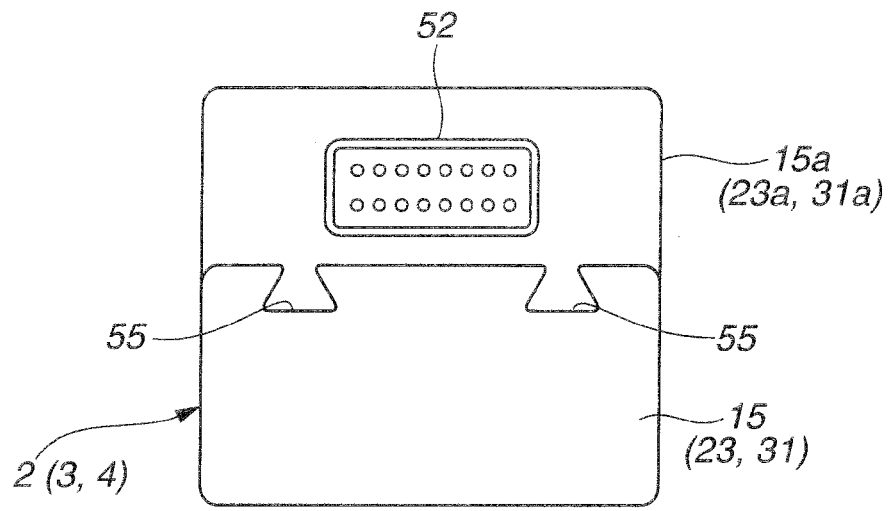
FIG. 6 is a front view showing the flexible endoscope apparatus, the rigid endoscope apparatus, or the monitor holder including a connector section according to the first embodiment.
Figure 7:
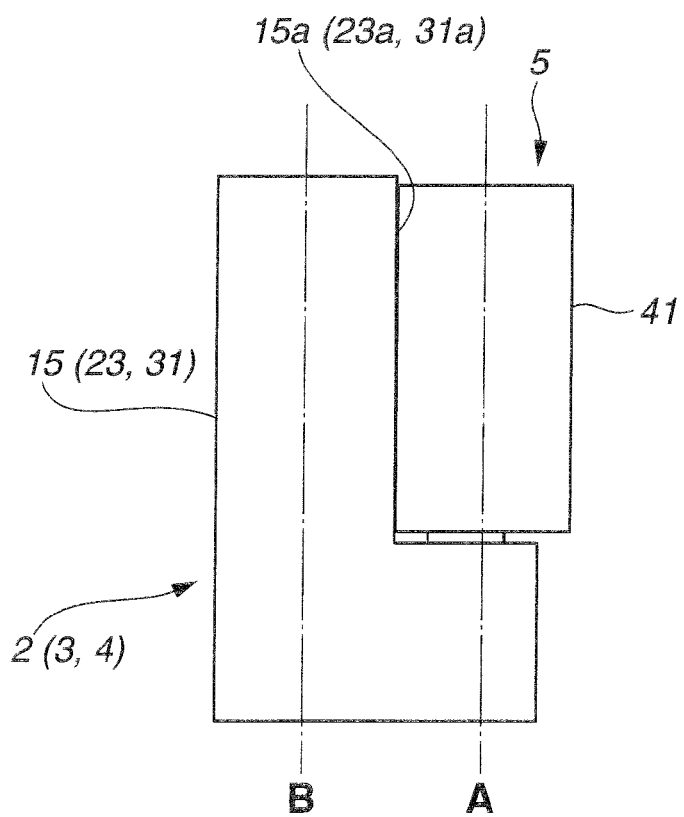
FIG. 7 is a side view showing a state in which the display device is placed on the flexible endoscope apparatus, the rigid endoscope apparatus, or the monitor holder according to the first embodiment.
Figure 8:
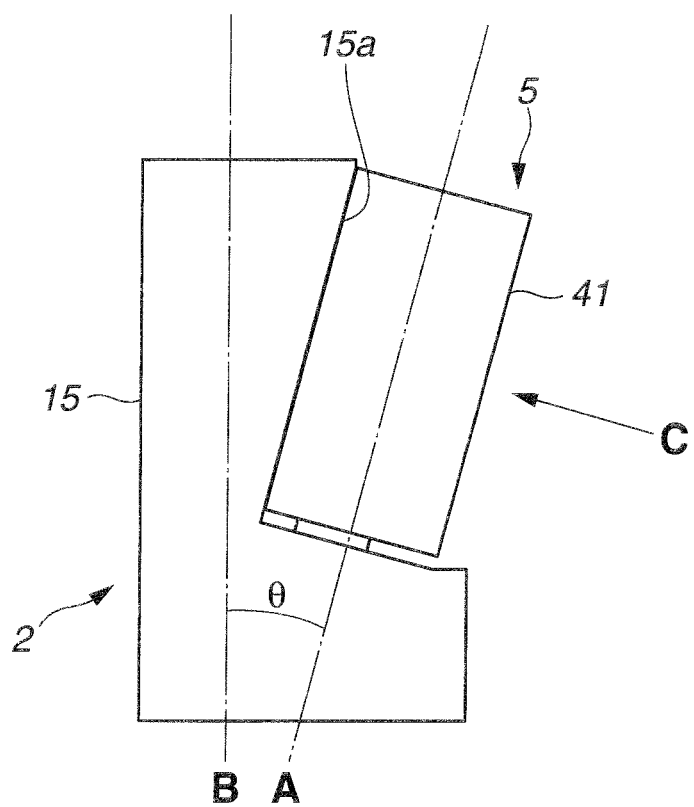
FIG. 8 is a side view showing a modification and showing a state in which the display device is placed on the flexible endoscope apparatus according to the first embodiment.
Figure 9:
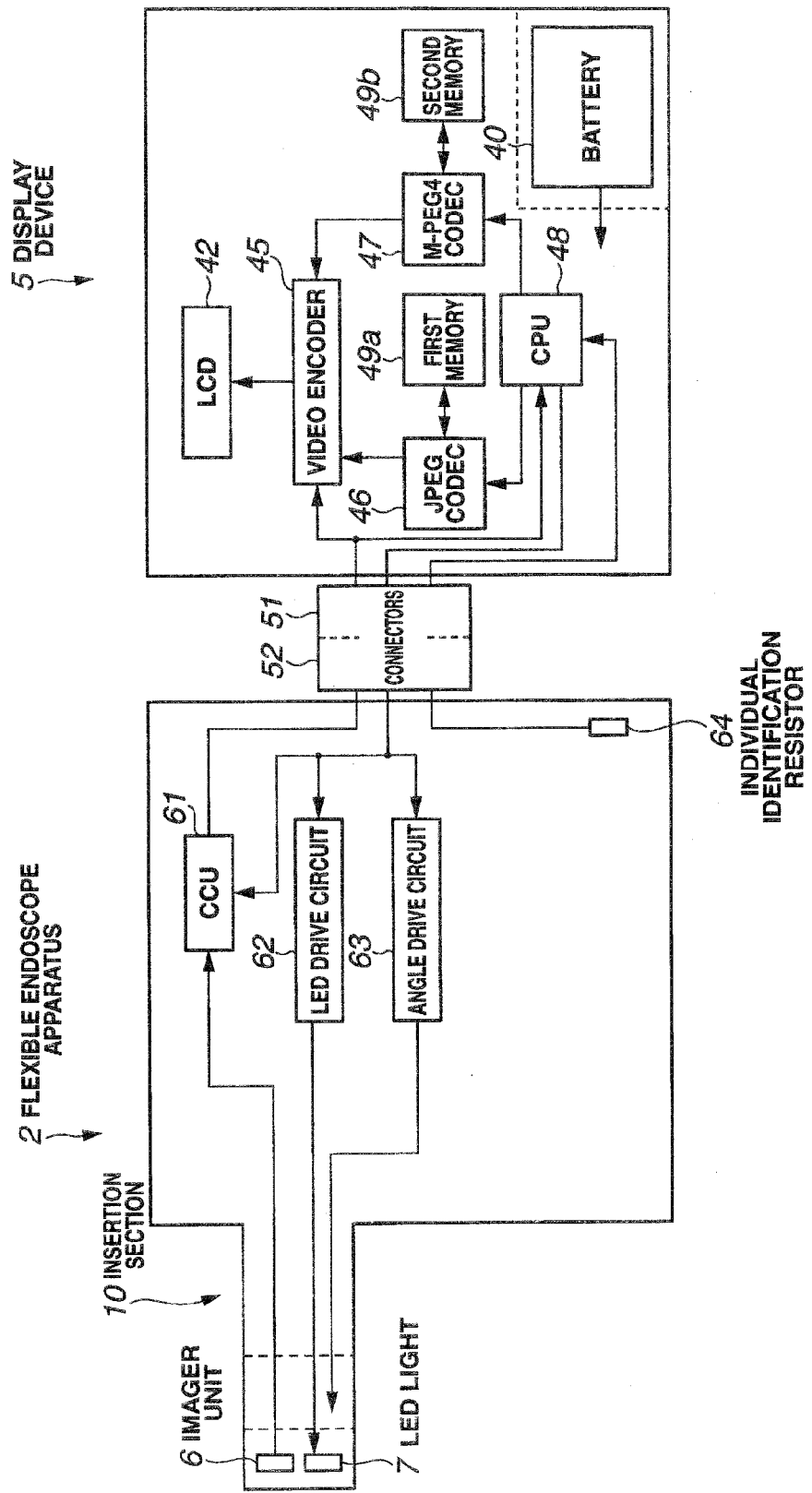
FIG. 9 is a block diagram showing internal configurations of the display device and the flexible endoscope apparatus connected via connector sections according to the first embodiment.
Figure 10:
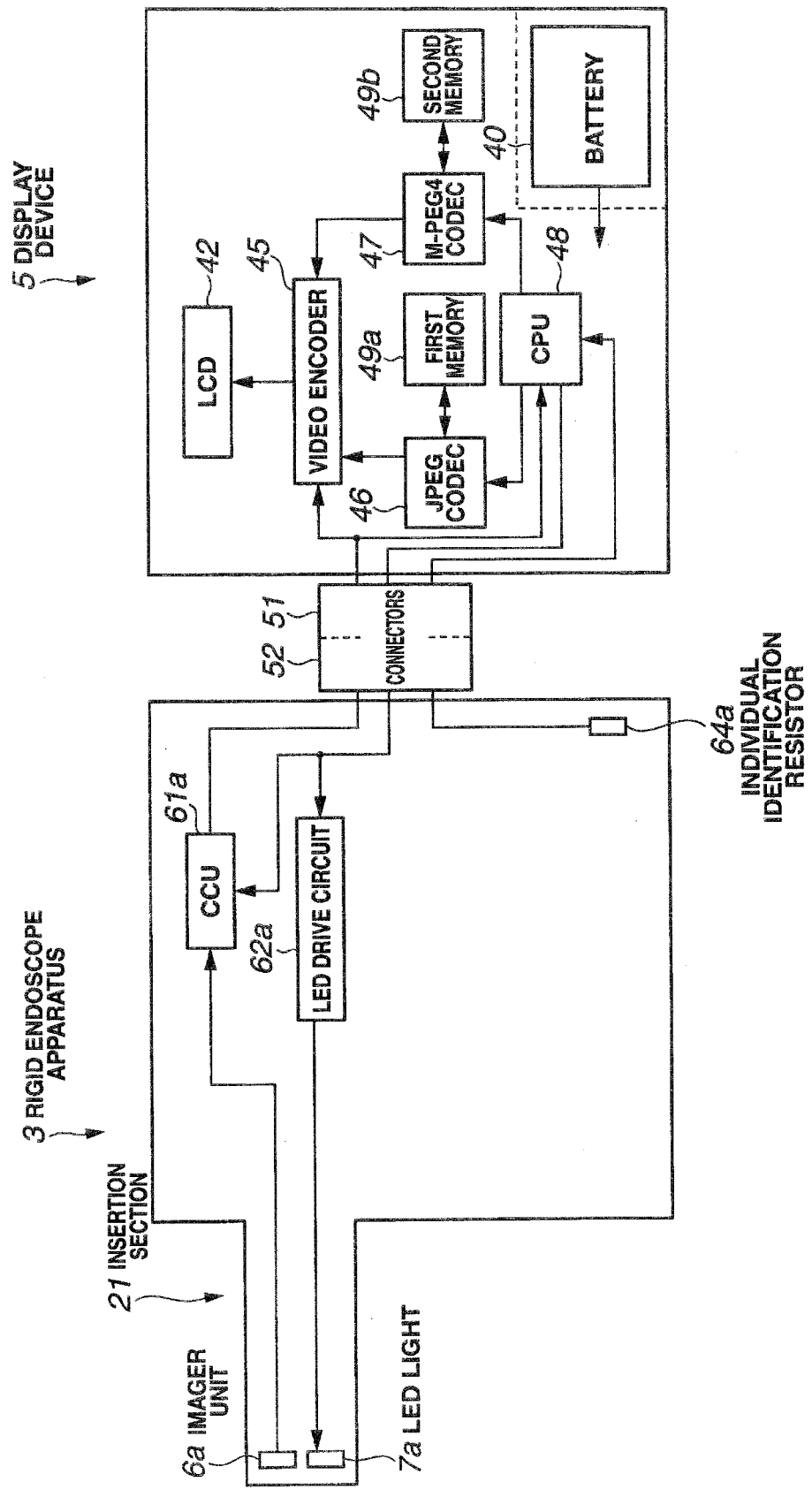
FIG. 10 is a block diagram showing internal configurations of the display device and a first rigid endoscope apparatus connected via the connector sections according to the first embodiment.
Figure 11:
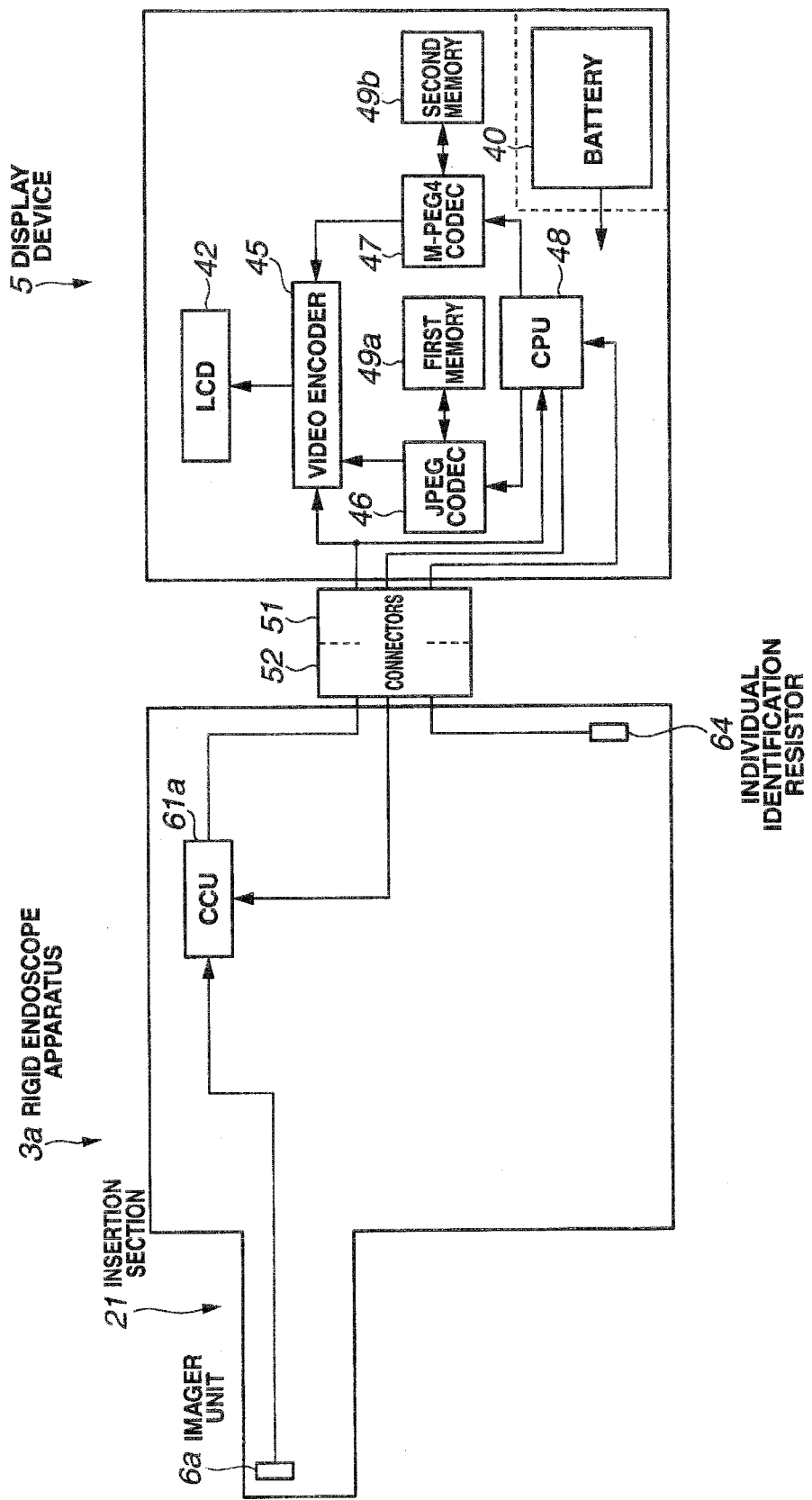
FIG. 11 is a block diagram showing internal configurations of the display device and a second rigid endoscope apparatus connected via the connector sections according to the first embodiment.
Figure 12:
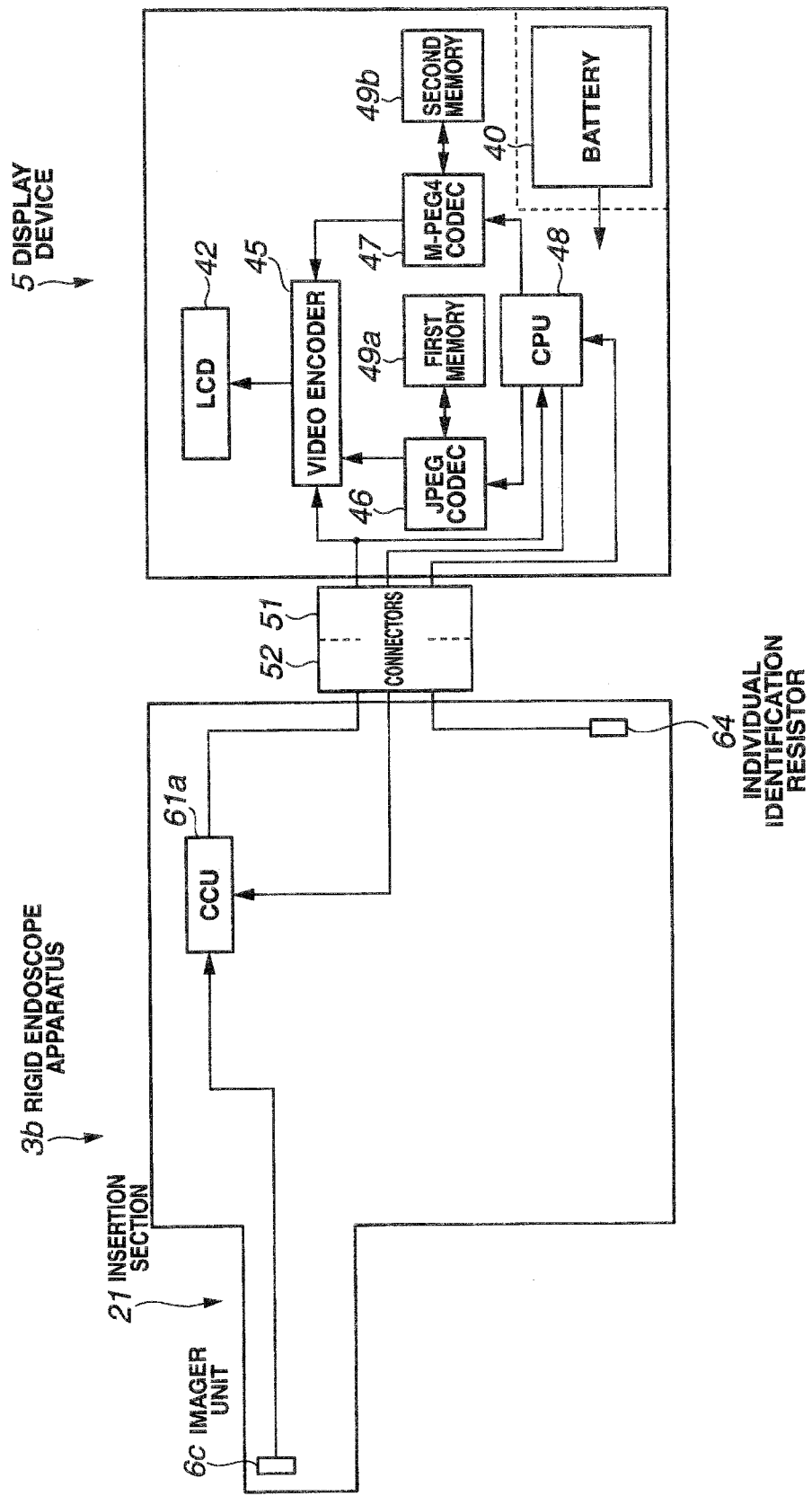
FIG. 12 is a block diagram showing internal configurations of the display device and a third endoscope apparatus connected via the connector sections according to the first embodiment.
Figure 13:
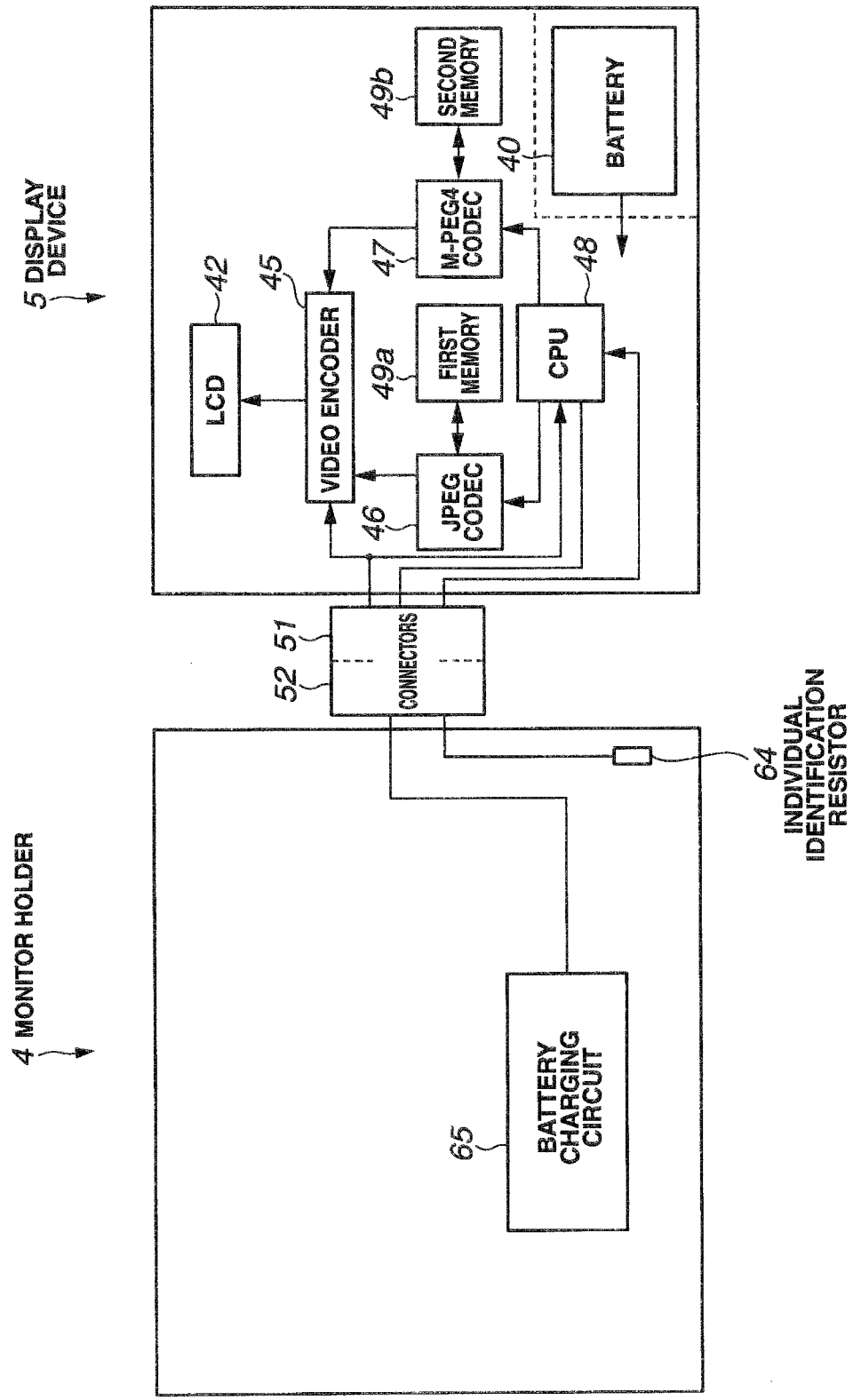
FIG. 13 is a block diagram showing internal configurations of the display device and the monitor holder connected via the connector sections according to the first embodiment.
Figure 14:
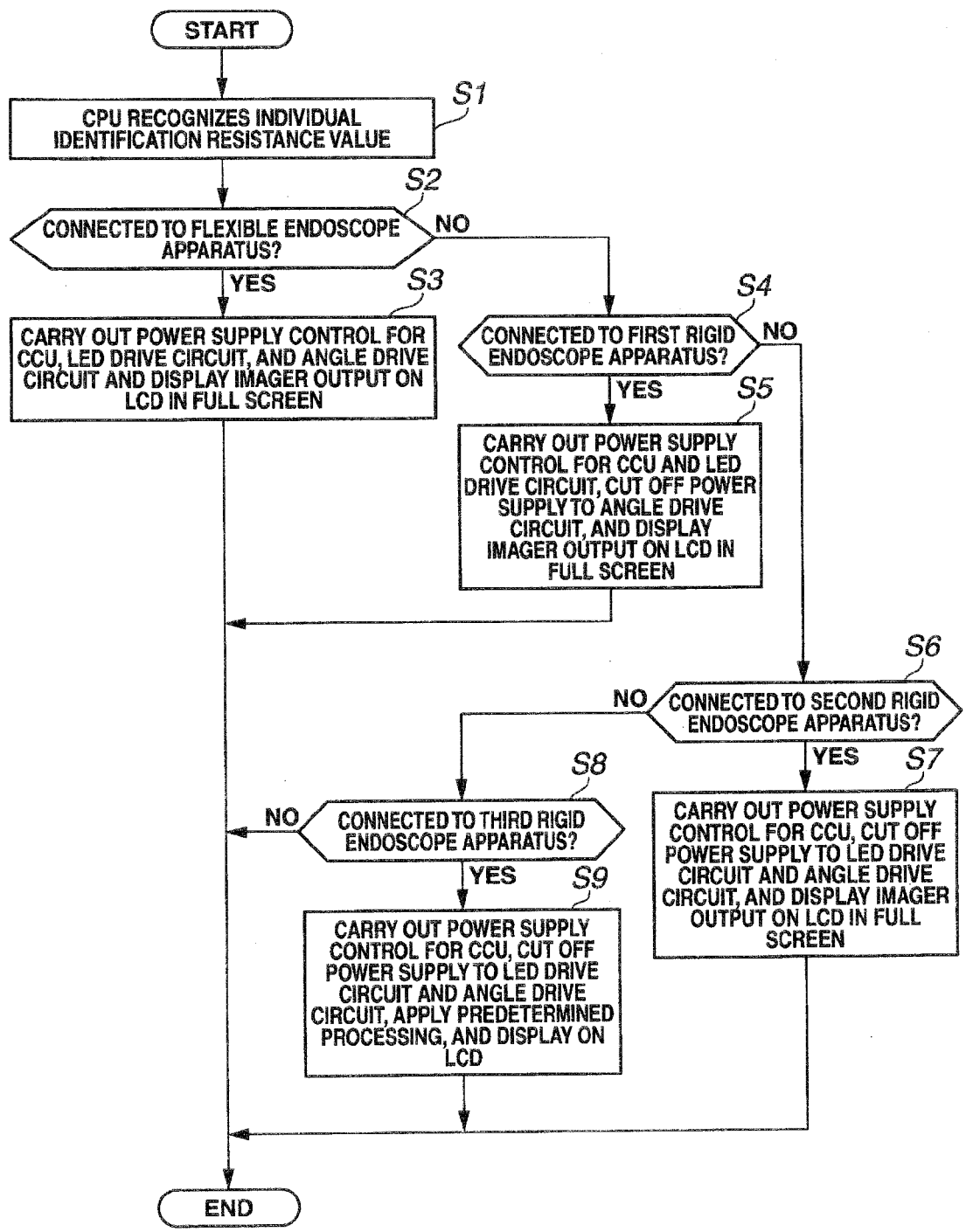
FIG. 14 is a processing flowchart by a control section of the display device according to the first embodiment.
Figure 15:
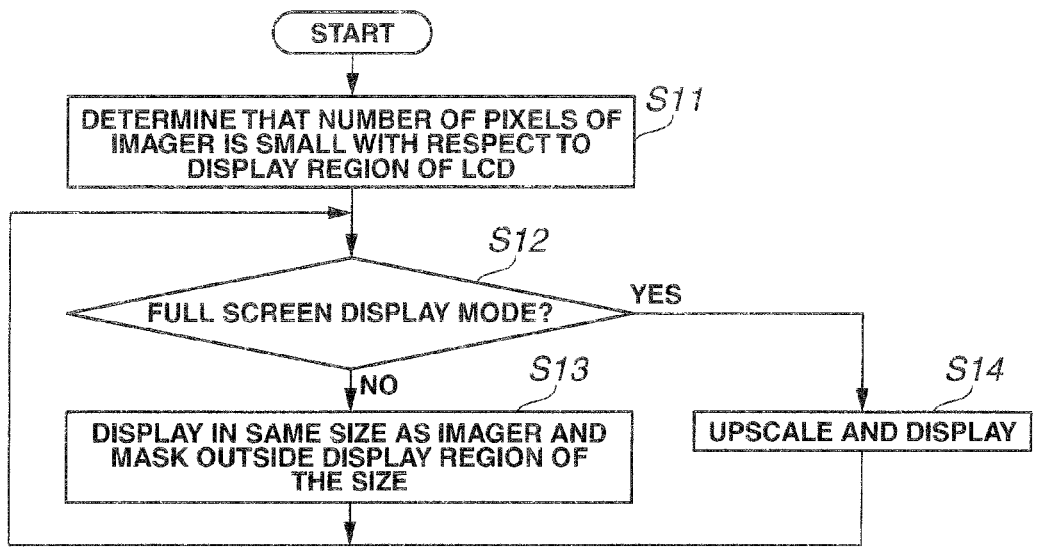
FIG. 15 shows sub-processing of FIG. 14 and is a processing flowchart by the control section of the display device according to the first embodiment.
Figure 16:
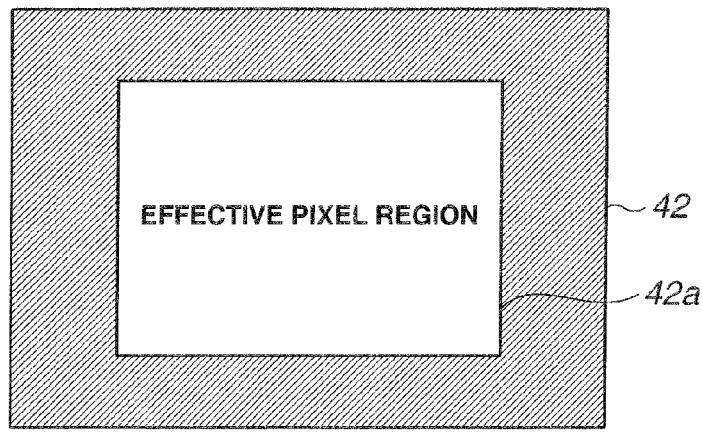
FIG. 16 is a plan view showing a display screen of an LCD according to the first embodiment.
Figure 17:
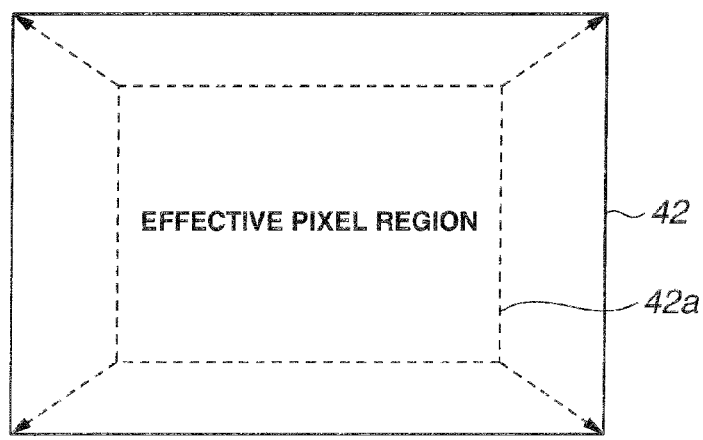
FIG. 17 is a plan view showing the display screen of the LCD during a full screen display mode according to the first embodiment.

FIGS. 1 to 8 relate to the first embodiment of the present invention. FIG. 1 is a perspective view showing an overall configuration of the endoscope system, FIG. 2 is a perspective view showing a state in which a display device is placed on a flexible endoscope apparatus, FIG. 3 is a perspective view showing a state in which the display device is placed on a rigid endoscope apparatus, FIG. 4 is a perspective view showing a state in which the display device is placed on a monitor holder, FIG. 5 is a sectional view showing a state in which the display device is placed on the flexible endoscope apparatus, the rigid endoscope apparatus, or the monitor holder, FIG. 6 is a front view showing the flexible endoscope apparatus, the rigid endoscope apparatus, or the monitor holder including a connector section, FIG. 7 is a side view showing a state in which the display device is placed on the flexible endoscope apparatus, the rigid endoscope apparatus, or the monitor holder, FIG. 8 is a side view showing a modification and showing a state in which the display device is placed on the flexible endoscope apparatus, FIG. 9 is a block diagram showing internal configurations of the display device and the flexible endoscope apparatus connected via the connector sections, FIG. 10 is a block diagram showing internal configurations of the display device and a first rigid endoscope apparatus connected via the connector sections, FIG. 11 is a block diagram showing internal configurations of the display device and a second rigid endoscope apparatus connected via the connector sections, FIG. 12 is a block diagram showing internal configurations of the display device and a third endoscope apparatus connected via the connector sections, FIG. 13 is a block diagram showing internal configurations of the display device and the monitor holder connected via the connector sections, FIG. 14 is a processing flowchart by a control section of the display device, FIG. 15 shows sub-processing of FIG. 14 and is a processing flowchart by the control section of the display device, FIG. 16 is a plan view showing a display screen of an LCD, and FIG. 17 is a plan view showing the display screen of the LCD during a full screen display mode.

As shown in FIG. 1, an endoscope system 1 according to this embodiment includes a flexible endoscope apparatus (hereinafter referred to as flexible endoscope) 2, which is a first apparatus and includes a flexible insertion section 10, a rigid endoscope apparatus (hereinafter referred to as rigid endoscope) 3, which is a second apparatus and includes a rigid insertion section 21, a monitor holder 4 of a monitor power supply apparatus functioning as a charging apparatus, which is a third apparatus, and a display device 5, which is a monitor display device including an LCD functioning as a monitor screen that can be placed on the flexible endoscope 2, the rigid endoscope 3, and the monitor holder 4 in common.

The flexible endoscope 2 mainly includes the insertion section 10, a bend preventing portion 14 provided at a proximal end of the insertion section 10, a monitor placing section 15 from which this bend preventing portion 14 and the insertion section 10 are extended forward and on which the display device 5 is placed, a bending operation section 16 provided continuously to the monitor placing section 15 and including a bending operation lever 17, and a grasping section 18 extending from a proximal end of the bending operation section 16. The monitor placing section 15, the bending operation section 16, and the grasping section 18 form an operation section in the flexible endoscope 2.

The insertion section 10 mainly includes a distal end portion 11 incorporating an imager unit, which is an image pickup apparatus such as a CCD or a CMOS, and illuminating means such as an LED light not shown in the figure, a bending section 12 operated to be instructed to bend by the bending operation lever 17, and a flexible tube section 13 having predetermined flexibility. The insertion section 10 is provided continuously to a front surface of the monitor placing section 15 via the bend preventing portion 14 arranged at a proximal end of the flexible tube section 13.

The monitor placing section 15 includes a monitor placing surface 15a formed as a plane in order to place the display device 5 in an upper part thereof and a monitor contact section 15b formed as a stepped section to have a surface orthogonal to this monitor placing surface 15a. In this monitor placing surface 15a, two engaging recesses 55 for fixing the display device 5 are formed in a longitudinal direction.

In the bending operation section 16, although not shown in the figure, an electric bending mechanism that electrically pulls and loosens plural bending operation wires, which are inserted through the insertion section 10 and the monitor placing section 15, to bend the bending section 12 is incorporated. The electric bending mechanism pulls and loosens the plural bending operation wires according to a tilt of the bending operation lever 17. The grasping section 18 forms a handle section grasped by the user.

In the rigid endoscope 3, an imager unit, which is an image pickup apparatus such as a CCD or a CMOS, and illuminating means such as an LED light not shown in the figure are incorporated at a distal end portion of the rigid insertion section 21. This insertion section 21 is provided continuously to a front surface of a monitor placing section 23 via a bend preventing portion 22.

The monitor placing section 23 also includes a monitor placing surface 23a formed as a plane in order to place the display device 5 in an upper part thereof. The two engaging recesses 55 for fixing the display device 5 are also formed in the longitudinal direction on this monitor placing surface 23a. The monitor placing section 23 includes a convex section 24 having a surface orthogonal to the monitor placing surface 23a. A folding-type stand 25 for setting is provided on a lower surface of the monitor placing section 23.

The monitor holder 4 includes a monitor placing section 31 on which a folding-type stand 33 for setting is provided on a lower surface. A not-shown AC adapter is detachably connectable to this monitor placing section 31. This monitor placing section 31 also includes a monitor placing surface 31a formed as a plane in order to place the display device 5 in an upper part thereof. In this monitor placing surface 31a, the two engaging recesses 55 for fixing the display device 5 are also formed in the longitudinal direction. The monitor placing section 31 also includes a convex section 32 having a surface orthogonal to the monitor placing surface 23a.

The display device 5 includes a housing section 41. The LCD 42, which is a monitor screen, and various operation switches 43 and 44 are disposed on an upper surface of this housing section 41. The housing section 41 includes a connector section 51 provided on a side surface parallel to a lower side in a display direction of the LCD 42 and a convex section 41a provided on a side surface parallel to a left side in the display direction of the LCD 42.

This display device 5 is configured such that the apparatuses, i.e., the flexible endoscope 2, the rigid endoscope 3, and the monitor holder 4 can place the display device 5 thereon in common. In other words, as shown in FIGS. 2 to 4, the endoscope system 1 according to this embodiment is configured to detachably place the common display device 5 on the apparatuses, i.e., the flexible endoscope 2, the rigid endoscope 3, and the monitor holder 4.

Engaging projections 56 (see FIG. 5) provided on a rear surface of the display device 5 are engaged to be slid from a front to a rear into engaging recesses 55 formed in each monitor placing surface 15a, 23a, or 31a of the apparatus, i.e., the flexible endoscope 2, the rigid endoscope 3, or the monitor holder 4, whereby the display device 5 is placed on the monitor placing surface 15a, 23a, or 31a of an apparatus desired by the user.

Specifically, in the display device 5, as shown in FIG. 5, the two engaging projections 56 are formed along the longitudinal direction on a rear surface on an opposite side of a surface on which the LCD 42 is disposed. The engaging projections 56 are formed in a substantially triangular shape in a cross section widened on a projecting side. The engaging recesses 55 are formed in a substantially triangular shape in a cross section having substantially the same shape as the engaging projections 56 (see FIG. 6).

As explained above, the two engaging projections 56 engage with the two engaging recesses 55 of the flexible endoscope 2, the rigid endoscope 3, or the monitor holder 4. Therefore, the display device 5 is fixed with up, down, left, and right directions of the LCD 42 defined on the monitor placing surfaces 15a, 23a, and 31a on which the display device 5 is placed. The display device 5 is prevented from falling off from the flexible endoscope 2, the rigid endoscope 3, or the monitor holder 4.

Hooking sections such as claws may be provided in the display device 5 and hooked sections hooked by the hooking sections may be provided in the flexible endoscope 2, the rigid endoscope 3, and the monitor holder 4 to fix the display device 5 to define the up, down, left, and right directions of the LCD 42. A configuration same as a so-called a tripod for fixing a camera with attachment screws may be adopted in which screw grooves are provided in the display device 5 and a fixing screw mechanism for fixing a state in which the display device 5 is placed on the flexible endoscope 2, the rigid endoscope 3, or the monitor holder 4 is provided.

In the display device 5, as shown in FIG. 5, the housing section 41 has a width dimension d1 larger than a width dimension d2 of the monitor placing section 15 of the flexible endoscope 2. This width dimension d1 is larger than width dimensions d3 and d4 of the monitor placing sections 23 and 31 of the rigid endoscope 3 and the monitor holder 4. In other words, even if the width dimension d1 of the housing section 41 of the display device 5 is variously changed according to various sizes of the LCD 42 at screen aspect ratios 4:3 and 16:9, it is possible to place the display device 5 on the monitor placing surfaces 15a, 23a, and 31a.

When the display device 5 is mounted on the monitor placing surfaces 15a, 23a, and 31a of the flexible endoscope 2, the rigid endoscope 3, and the monitor holder 4 to be slid from the front to the rear until the display device 5 comes into contact with the monitor contact section 15b and front surfaces of the convex sections 24 and 32, the connector section 51 provided on a side surface on a rear side is electrically connected to connector sections 52 respectively provided on front surfaces of the monitor contact section 15b and the convex sections 24 and 32. In other words, in the flexible endoscope 2, the rigid endoscope 3, and the monitor holder 4, common connector sections 52 forming a pair with the connector section 51 of the display device 5 are respectively disposed on the front surfaces of the monitor contact section 15b and the convex sections 24 and 32.

As shown in FIG. 7, the display device 5 is placed on the monitor placing sections 15, 23, and 31 of the flexible endoscope 2, the rigid endoscope 3, and the monitor holder 4 such that a center axis (an axis parallel to a display screen of the LCD 42) A of the display device 5 and a longitudinal axis (an axis parallel to the monitor placing surfaces 15a, 23a, and 31a) B of the monitor placing sections 15, 23, and 31 are parallel to each other.

As shown in FIG. 8, the display device 5 may be placed on the monitor placing section 15 of only the flexible endoscope 2 such that the center axis (the axis parallel to the display screen of the LCD 42) A of the display device 5 and the longitudinal axis (the axis parallel to the monitor placing surface 15a) B of the monitor placing section 15 have a predetermined angle θ. In other words, the monitor placing surface 15a is formed as a slope having the predetermined angle θ with respect to the longitudinal axis B of the monitor placing section 15. Since this flexible endoscope 2 is grasped by the user during use such as bending operation of the bending section 12, the flexible endoscope 2 is formed such that the user faces the LCD 42 of the display device 5 (a state in which an eye line C direction is substantially perpendicular to the display screen of the LCD 42).

Internal configurations and electric connections in a state in which the display device 5 is placed on the flexible endoscope 2, the rigid endoscope 3, and the monitor holder 4 of the endoscope system 1 are explained below with reference to FIGS. 9 to 11.

First, the flexible endoscope 2 and the display device 5 are explained.

As shown in FIG. 9, in the flexible endoscope 2, for example, an imager unit 6 having display resolution of 640× 480 size (VGA) and an LED light 7 are disposed at the distal end portion 11 of the insertion section 10. In the flexible endoscope 2, a CCU (camera control unit) 61, an LED drive circuit 62, an angle drive circuit 63, and an individual identification resistor 64 are incorporated.

The imager unit 6 is electrically connected to the CCU 61. The CCU 61 is a unit for supplying electric power and a driving signal to the imager unit 6 and applying various kinds of video processing (e.g., AD conversion, CDS, PGA, RGB interpolation processing, gamma correction, contour correction, and noise reduction) to an output signal of the imager unit 6 and outputting the output signal. The LED 7 is electrically connected to the LED drive circuit 62. The LED drive circuit 62 is an electric circuit for supplying driving power to the LED and adjusting an LED light amount. The angle drive circuit 63 is an electric circuit for bending the bending section 12 of the insertion section 10.

In the display device 5, besides the LCD 42 {display resolution (VGA)}, a detachable battery 40, a video encoder 45, a JPEG codec 46, an MPEG4 codec 47, a CPU 48, which is a control section, a first memory 49a, and a second memory 49b are incorporated.

The video encoder 45 causes the LCD 42 to display a live video picked up by the imager unit 6 and inputted from the CCU 61 of the flexible endoscope 2. The video encoder 45 is connected to the JPEG codec 46 and the MPEG4 codec 47. The video encoder 45 causes the LCD 42 to display, as a moving image or a still image, image data stored (recorded) in the first memory 49a connected to the JPEG codec 46 or the second memory 49b connected to the MPEG4 codec 47. Display selection of the live video, the moving image, and the still image is controlled by the CPU 48.

The JPEG codec 46 is controlled by the CPU 48. The JPEG codec 46 compresses, into a JPEG system, image data picked up by the imager unit 6 and inputted from the CCU 61 of the flexible endoscope 2 via the connector sections 51 and 52 and stores (records) the image data in the first memory 49a. The JPEG codec 46 reads out image data in a JPEG format stored in the first memory 49a.

The MPEG4 codec 47 is controlled by the CPU 48. The MPEG4 codec 47 compresses, into an MPEG4 system, image data picked up by the imager unit 6 and inputted from the CCU 61 of the flexible endoscope 2 via the connector sections 51 and 52 and stores (records) the image data in the second memory 49b. The MPEG4 codec 47 reads out image data in an MPEG4 format stored (recorded) in the second memory 49b.

The CPU 48 recognizes, with the individual identification resistor 64 detected via the connector sections 51 and 52, the connected apparatus, i.e., the flexible endoscope 2 and controls to drive the CCU 61, the LED drive circuit 62, and the angle drive circuit 63 incorporated in the flexible endoscope 2.

Next, the rigid endoscope 3 in a state in which the display device 5 is placed thereon is explained.

As shown in FIG. 10, in the rigid endoscope 3, as in the flexible endoscope 2, for example, an imager unit 6a having display resolution of 640×480 size (VGA) and an LED light 7a are disposed at the distal end portion of the insertion section 21. In the rigid endoscope 3, as in the flexible endoscope 2, a CCU (camera control unit) 61a, an LED drive circuit 62a, and the individual identification resistor 64a are incorporated. Since a bending section is not provided in the rigid endoscope 3, the rigid endoscope 3 does not include the angle drive circuit 63 for bending the bending section.

As in the flexible endoscope 2, the imager unit 6a is electrically connected to the CCU 61a. The LED 7a is electrically connected to the LED drive circuit 62a. In the rigid endoscope 3, the individual identification resistor 64 is a resistor for identifying an individual of the rigid endoscope 3. It goes without saying that the individual identification resistor 64 may be an RFID or the like as in the flexible endoscope 2 explained above.

The CCU 61a, the LED drive circuit 62a, and the individual identification resistor 64 are electrically connected to the CPU 48 and the video encoder 45 of the display device 5 via the pair of connector sections 51 and 52 electrically connected to each other.

The video encoder 45 of the display device 5 causes the LCD 42 to display a live video picked up by the imager unit 6a and inputted from the CCU 61a of the rigid endoscope 3. The video encoder 45 causes the LCD 42 to display a still image or a moving image outputted from the JPEG codec 46 or the MPEG4 codec 47. As in the flexible endoscope 2, the JPEG codec 46 compresses, into the JPEG system, image data picked up by the imager unit 6a and inputted from the CCU 61a of the rigid endoscope 3 via the connector sections 51 and 52 and stores (records) the image data in the first memory 49a. The JPEG codec 46 reads out image data in the JPEG format stored in the first memory 49a. The MPEG4 codec 47 compresses, into the MPEG4 system, image data picked up by the imager unit 6a and inputted from the CCU 61a of the rigid endoscope 3 via the connector sections 51 and 52 and stores (records) the image data in the second memory 49b. The MPEG4 codec 47 reads out image data in the MPEG4 format stored (recorded) in the second memory 49b.

The CPU 48 recognizes, with the individual identification resistor 64 detected via the connector sections 51 and 52, the connected apparatus, i.e., the rigid endoscope 3 and controls to drive the CCU 61a and the LED drive circuit 62a incorporated in the rigid endoscope 3.

Besides the rigid endoscope 3 including the internal configuration explained above, the display device 5 can also be placed on a rigid endoscope 3a not including the LED light 7a and the LED drive circuit 62a that drives the LED light 7a as shown in FIG. 11 and a rigid endoscope 3b including, for example, the imager unit 6a having display resolution of 320×240 size (QVGA) as shown in FIG. 12. In the following explanation, in some case, the rigid endoscope 3 shown in FIG. 10 is described as first rigid endoscope 3, the rigid endoscope 3a shown in FIG. 11 is described as second rigid endoscope 3a, and the rigid endoscope 3b shown in FIG. 12 is described as third endoscope 3b to distinguish the rigid endoscopes.

Next, the monitor holder 4 in a state in which the display device 5 is placed thereon is explained.

As shown in FIG. 13, the individual identification resistor 64 is incorporated in the monitor holder 4 as well. In the monitor holder 4, the individual identification resistor 64 is a resistor for identifying an individual of the monitor holder 4. It goes without saying that the individual identification resistor 64 may be an RFID or the like as in the flexible endoscope 2 and the rigid endoscope 3 explained above.

In the monitor holder 4, a battery charging circuit 65 that is electrically connected to the battery 40 in the display device 5 via the connector sections 51 and 52 and charges this battery 40 is incorporated. As explained above, a not-shown detachable AC adapter is connected to this monitor holder 4. The AC adapter supplies electric power for charging circuit driving. In the embodiment, the battery, which is a power supply source to the system, is mounted on the display device 5. However, the battery may be mounted on the flexible endoscope 2, the rigid endoscope 3 (3a or 3b), and the monitor holder 4.

In the endoscope system 1 according to this embodiment configured as explained above, the display device 5 is placed on the flexible endoscope 2 or the rigid endoscope 3 (3a or 3b) and the CPU 48 of the display device 5 recognizes the individual identification resistor 64 of the apparatus electrically connected via the connector sections 51 and 52. At this point, the CPU 48 of the display device 5 executes a control example based on flowcharts of FIGS. 14 and 15 according to the flexible endoscope 2 or the rigid endoscope 3 (3a or 3b).

Specifically, first, when the display device 5 is placed on the flexible endoscope 2 or the rigid endoscope 3 (3a or 3b), as shown in FIG. 14, the CPU 48 recognizes a resistance value of the individual identification resistor 64 of the connected apparatus via the connector sections 51 and 52 (S1).

Subsequently, the CPU 48 determines, from the recognized resistance value of the individual identification resistor 64, whether the display device 5 is connected to the flexible endoscope 2 (S2). At this point, when the CPU 48 determines that the resistance value of the individual identification resistor 64 is the flexible endoscope 2, the CPU 48 carries out power supply control to the CCU 61, the LED drive circuit 62, and the angle drive circuit 63 of the flexible endoscope 2, displays an imager output on the LCD 42 in a full screen (S3), and ends the processing.

After determining in the processing in step S2 that the resistance value of the individual identification resistor 64 is not the flexible endoscope 2, the CPU 48 determines whether the display device 5 is connected to the first rigid endoscope 3 (S4). At this point, when the CPU 48 determines that the resistance value of the individual identification resistor 64 is the first rigid endoscope 3, the CPU 48 carries out power supply control to the CCU 61a and the LED drive circuit 62a of the first rigid endoscope 3, cuts off power supply to the angle drive circuit 63 corresponding to the flexible endoscope 2, displays an imager output on the LCD 42 in a full screen (S5), and ends the processing.

After determining in the processing in step S4 that the resistance value of the individual identification resistor 64 is not the first rigid endoscope 3, the CPU 48 determines whether the display device 5 is connected to the second rigid endoscope 3a (S6), At this point, when the CPU 48 determines that the resistance value of the individual identification resistor 64 is the second rigid endoscope 3a, the CPU 48 also carries out power supply control to the CCU 61a and the LED drive circuit 62a of the second rigid endoscope 3a, cuts off power supply to the angle drive circuit 63 corresponding to the flexible endoscope 2, displays an imager output on the LCD 42 in a full screen (S7), and ends the processing.

After determining in the processing in step S6 that the resistance value of the individual identification resistor 64 is not the second rigid endoscope 3a, the CPU 48 determines whether the display device 5 is connected to the third rigid endoscope 3b (S8). When the CPU 48 determines that the resistance value of the individual identification resistor 64 is the third rigid endoscope 3b, the CPU 48 carries out power supply control to the CCU 61a of the third rigid endoscope 3b and cuts off power supply to the LED drive circuit 62a and the angle drive circuit 63 corresponding to the flexible endoscope 2. Further, the CPU 48 applies predetermined processing to an imager output of the LCD 42 and displays the imager output on the LCD 42 (S9) and ends the processing.

When the CPU 48 determines in the processing in step S8 that the resistance value of the individual identification resistor 64 is not the third rigid endoscope 3a, the CPU 48 ends the processing.

As explained above, the endoscope system 1 according to this embodiment controls, with the CPU 48 of the display device 5, power supply control to the internal configuration of the flexible endoscope 2 or the rigid endoscope 3 (3a or 3b) according to the flexible endoscope 2 or the rigid endoscope 3 (3a or 3b) on which the display device 5 is placed and to which the display device 5 is connected. Consequently, the endoscope system 1 performs the power supply only to necessary electric components in the flexible endoscope 2 or the rigid endoscope 3 (3a or 3b) to which the display device 5 is connected. Therefore, a configuration in which power consumption efficiency is high and power is saved can be obtained.

In the processing in step S9, as shown in FIG. 15, the CPU 48 determines that the number of pixels is small in the imager unit 6a having display resolution of QVGA included in the third rigid endoscope 3b with respect to a display region of the LCD 42 having a display region of VGA (S11), The CPU 48 determines whether a present mode is a full screen display mode (S12). In the display device 5, the user can change a mode of a display region displayed on the LCD 42 to the full screen display mode by operating either one of the plural operation switches 43 and 44 (see FIGS. 1 to 4).

When the CPU 48 determines in the processing in step S12 that the present mode is not the full screen display mode, as shown in FIG. 16, the CPU 48 displays, on the LCD 42, an output of the imager unit 6a in a size same as the display resolution (QVGA) of the imager unit 6a and masks a region other than an effective pixel region 42a (S13). The CPU 48 returns to the processing in step S12.

When the CPU 48 determines in the processing in step S12 that the present mode is the full screen display mode, as shown in FIG. 17, the CPU 48 up-scales the effective pixel region 42a of the imager unit 6a according to the display screen of the LCD 42 and displays the effective pixel region 42a (S14). The CPU 48 returns to the processing in step S12 again.

In this way, if the display device 5 is set to the full screen display mode, the display device 5 can (up-scale and) automatically display, as a full screen, for example, a photographed image including only effective pixels having the display resolution of QVGA on the display screen of the LCD 42 having the display resolution of VGA.

As explained above, the endoscope system 1 according to this embodiment includes the flexible endoscope 2, the rigid endoscope 3 (3a or 3b), or the monitor holder 4, which are the plural apparatuses having different functions, and includes the common display device 5 that can be placed on the apparatuses from a common (same) direction. In other words, the user can place the display device 5 on the flexible endoscope 2, the rigid endoscope 3 (3a or 3b), or the monitor holder 4 from the common direction in which the display device 5 faces the apparatus.

Consequently, by using a high-function endoscope such as the flexible endoscope 2 including the bending section, a low-function endoscope such as the rigid endoscope 3, 3a, or 3b, and the monitor holder 4 including the charging function, the user can properly use the apparatuses according to work suitable for an inspection purpose, i.e., a place where an inspection is more easily performed when the bending section is present in a flexible insertion section and a place where an inspection is more easily performed with a rigid insertion section. Further, the user can also charge the display device 5 while checking a photographed video by placing the display device 5 on the monitor holder 4 in a work site.

Since the user can perform an inspection in a state in which the display device 5 is placed on the flexible endoscope 2, the rigid endoscope 3 (3a or 3b), or the monitor holder 4 during inspection work, the user can perform various kinds of operation of the apparatuses without taking the user's eyes off the display device 5.

As a result, the endoscope system 1 according to this embodiment can improve inspection efficiency in the work site.

Second Embodiment

Next, an endoscope system according to a second embodiment of the present invention is explained. In the following explanation, components same as those of the endoscope system 1 according to the first embodiment explained above are denoted by the same reference numerals and signs and specific explanation of the components is omitted.

Figure 18:
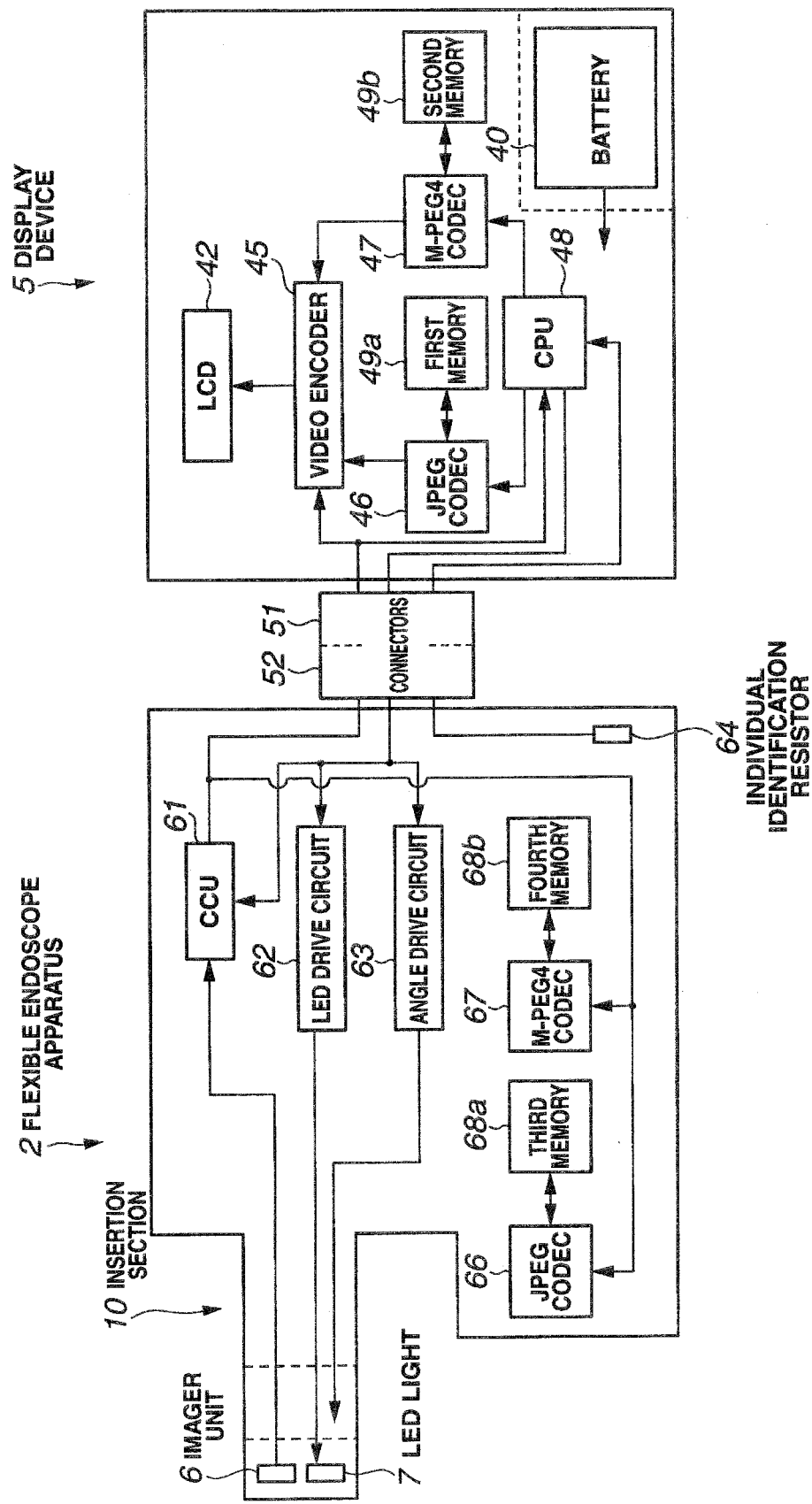
FIG. 18 is a block diagram showing internal configurations of a display device and a flexible endoscope apparatus connected via connector sections according to a second embodiment.
Figure 19:
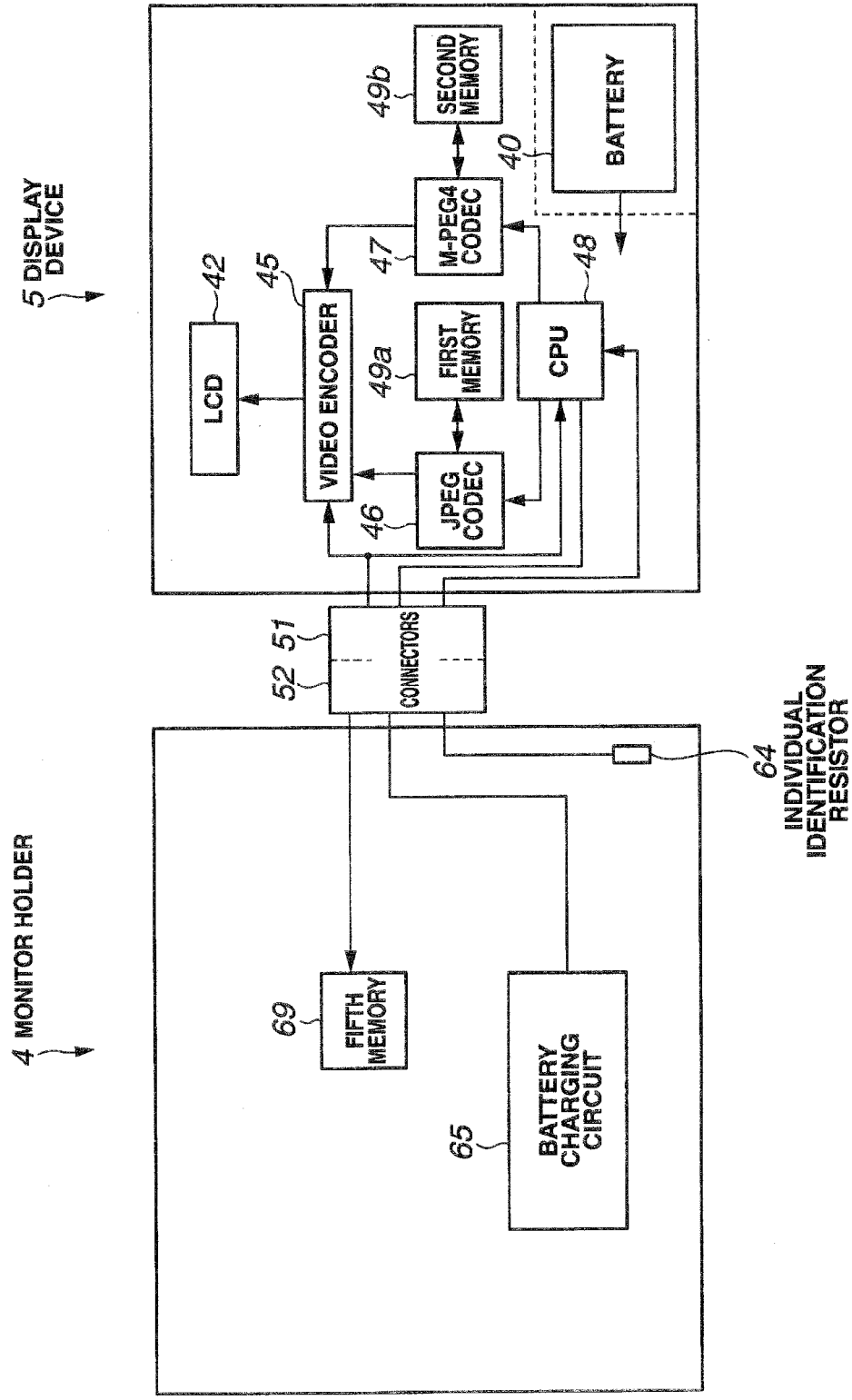
FIG. 19 is a block diagram of internal configurations of the display device and a monitor holder connected via the connector sections according to the second embodiment.
Figure 20:
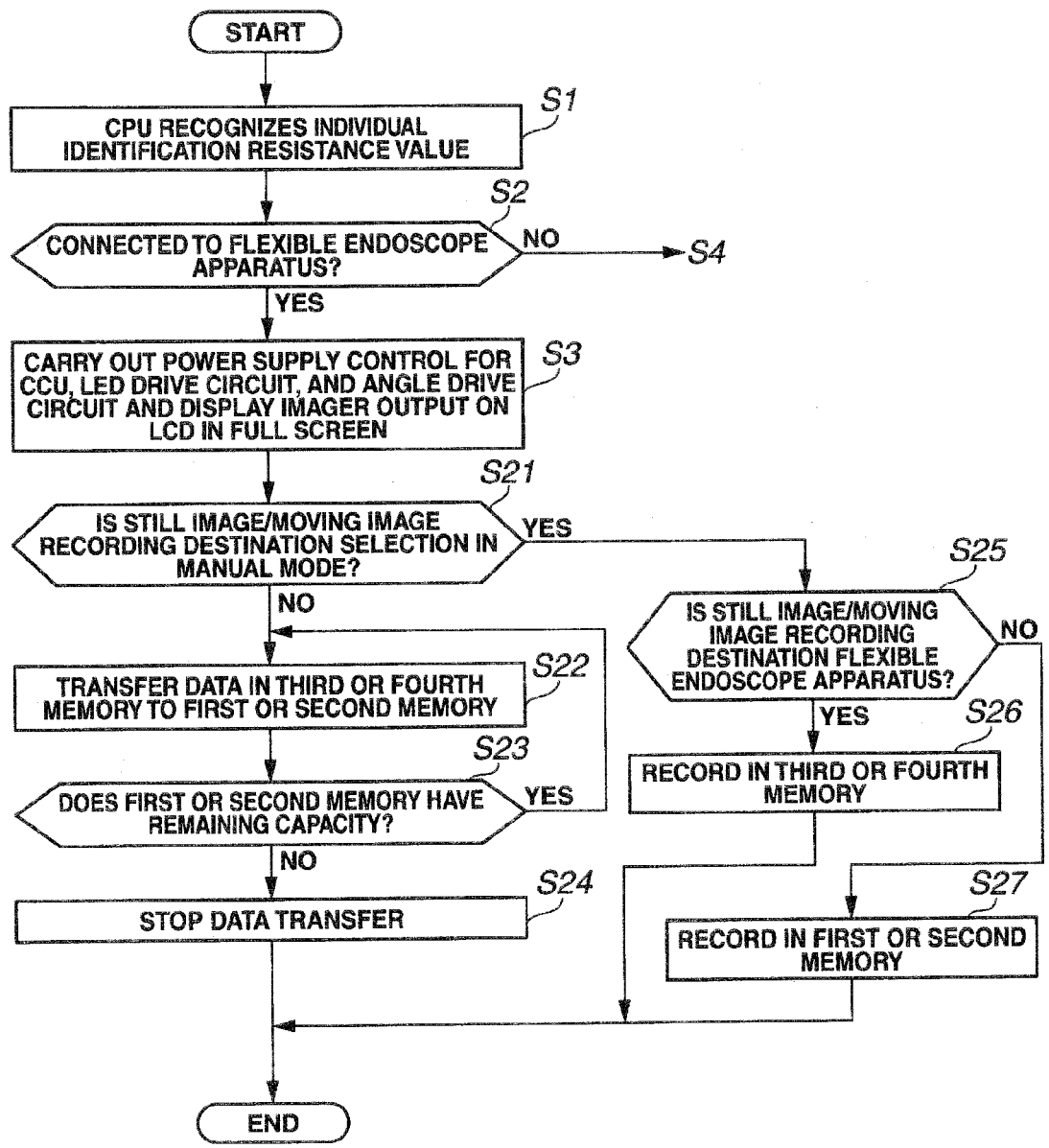
FIG. 20 is a processing flowchart by a control section of the display device placed on the flexible endoscope apparatus according to the second embodiment.
Figure 21:
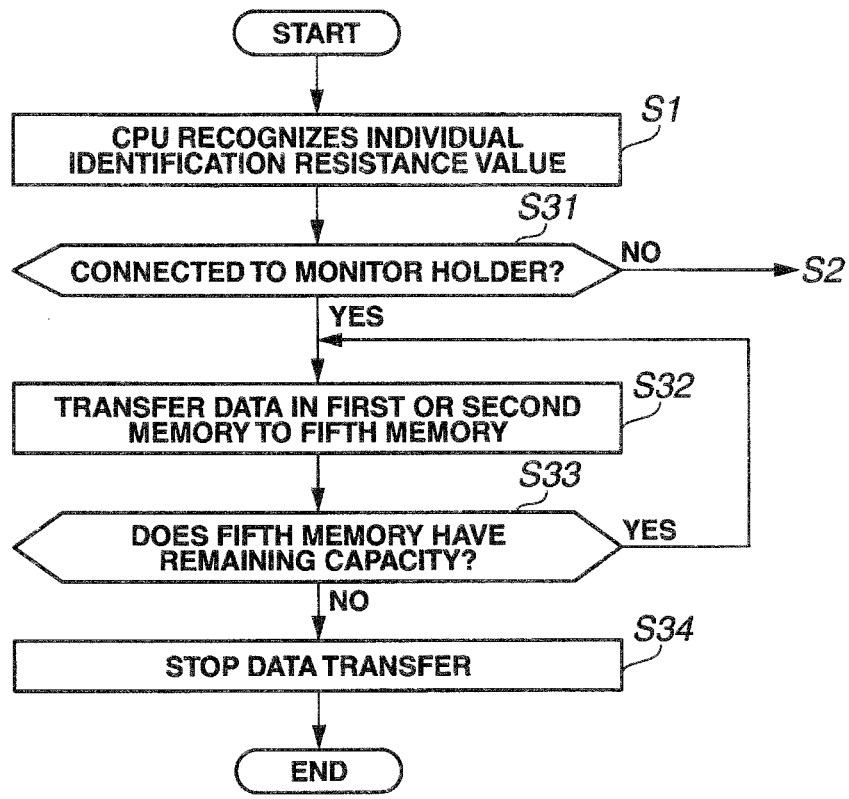
FIG. 21 is a processing flowchart by the control section of the display device placed on the monitor holder according to the second embodiment.

FIGS. 18 to 21 relate to the second embodiment of the present invention. FIG. 18 is a block diagram showing internal configurations of a display device and a flexible endoscope apparatus connected via connector sections. FIG. 19 is a block diagram of internal configurations of the display device and a connector monitor holder connected via the connector sections. FIG. 20 is a processing flowchart by a control section of the display device placed on the flexible endoscope apparatus. FIG. 21 is a processing flowchart by the control section of the display device placed on the monitor holder.

As shown in FIG. 18, in the flexible endoscope 2 according to this embodiment, a JPEG codec 66 to which image data picked up by the imager unit 6a is transferred from the CCU 61, a third memory 68a that stores (records) the image data compressed into the JPEG system by this JPEG codec 66, an MPEG4 codec 67 to which image data picked up by the imager unit 6a is transferred from the CCU 61, and a fourth memory 68b that stores (records) the image data compressed into the MPEG4 system by this MPEG4 codec 67 are disposed on an inside. The JPEG codec 66, the third memory 68a, the MPEG4 codec 67, and the fourth memory 68b may be provided on an inside of the rigid endoscope 3 (3a or 3b).

In the monitor holder 4 according to this embodiment, a fifth memory 69 that stores (records) image data compressed by the JPEG system or the MPEG4 system is disposed. This fifth memory 69 is electrically connected to the JPEG codec 46 and the MPEG4 codec 47 via the connector sections 51 and 52 and via the CPU 48 of the display device 5.

In endoscope system 1 according to this embodiment configured as explained above, the display device 5 is placed on the flexible endoscope 2 or the monitor holder 4, The CPU 48 of the display device 5 recognizes the individual identification resistor 64 of the apparatus electrically connected via the connector sections 51 and 52, The CPU 48 of the display device 5 executes a control example based on flowcharts of FIGS. 20 and 21 according to the flexible endoscope 2 or the monitor holder 4.

Specifically, as shown in FIG. 18, in a state in which the display device 5 is placed on the flexible endoscope 2, in addition to the control example of the flowchart of FIG. 14, as shown in FIG. 20, after the processing in step S3, the CPU 48 of the display device 5 determines whether selection of a still image or moving image recording destination is in a manual mode (S21). In the endoscope system 1 according to this embodiment, a user can select the manual mode or an automatic mode for the selection of a still image or moving image recording destination by operating either one of the plural operation switches 43 and 44 (see FIGS. 1 to 4) of the display device 5.

When the CPU 48 determines in the processing in step S21 that the selection of a still image or moving image recording destination is not the manual mode, the CPU 48 transfers image data stored (recorded) in the third memory 68a or the fourth memory 68b of the flexible endoscope 2 to the first memory 49a or the second memory 49b of the display device 5 (S22).

At this point, the CPU 48 determines whether a memory remaining capacity of the first memory 49a or the second memory 49b is present (>0/zero) or not (=0/zero) (S23). When a memory remaining capacity is absent (=0/zero), the CPU 48 stops the transfer of the image data (S24) and ends the processing. On the other hand, when a memory remaining capacity is present (>0/zero), the CPU 48 returns to step S22 and continues the processing.

When the selection of a still image or moving image recording destination is the manual mode in the processing in step S21, the CPU 48 determines whether the flexible endoscope 2 is selected as the still image or moving image recording destination (S25).

When the CPU 48 determines in the processing in step S25 that the selection of a still image or moving image recording destination is the flexible endoscope 2, the CPU 48 stores (records) image data picked up by the imager unit 6a in the third memory 68a or the fourth memory 68b of the flexible endoscope 2 (S26). When the selection of a still image or moving image recording destination is not the flexible endoscope 2, the CPU 48 stores (records) the image data in the first memory 49a or the second memory 49b of the display device 5 (S27) and ends the processing.

On the other hand, when the CPU 48 determines in the processing in step S25 that the selection of a still image or moving image recording destination is not the flexible endoscope 2, the CPU 48 stores (records) the image data picked up by the imager unit 6a only in the first memory 49a or the second memory 49b of the display device 5 (S27) and ends the processing.

As shown in FIG. 19, in a state in which the display device 5 is placed on the monitor holder 4, after the processing in step S1 of the flowchart of FIG. 14, the CPU 48 of the display device 5 determines from the recognized resistance value of the individual identification resistor 64 whether the display device 5 is connected to the monitor holder 4 (S31). When the CPU 48 determines that the display device 5 is not connected to the monitor holder 4, the CPU 48 shifts to the processing in step S2 of the flowchart of FIG. 14.

When the CPU 48 determines that the display device 5 is connected to the monitor holder 4, the CPU 48 transfers the image data stored (recorded) in the first memory 49a or the second memory 49b of the display device 5 to the fifth memory 69 of the monitor holder 4 (S32).

At this point, the CPU 48 determines whether a memory remaining capacity of the fifth memory 69 is present (>0) or not (=0) (S33). When a memory remaining capacity is absent (=0), the CPU 48 stops the transfer of the image data (S24) and ends the processing. On the other hand, when a memory remaining capacity is present (>0), the CPU 48 returns to step S32 and continues the processing.

As explained above, in the endoscope system 1 according to this embodiment, the third and fourth memories 68a and 68b are provided in the flexible endoscope 2 and the fifth memory 69 is provided in the monitor holder 4. Image data can be stored (recorded) in the third and fourth memories 68a and 68b and the fifth memory 69 besides the display device 5.

By adopting such a configuration, in addition to the effects of the first embodiment, the endoscope system 1 can transfer, during an inspection, image data photographed in the past stored in the first memory 49a or the second memory 49b in the display device 5 to the third and fourth memories 68a and 68b in the flexible endoscope 2 or the fifth memory 69 in the monitor holder 4 and secure a memory remaining capacity of the first memory 49a or the second memory 49b.

Image data stored (recorded) in the third and fourth memories 68a and 68b in the flexible endoscope 2 or the fifth memory 69 in the monitor holder 4 is read by the CPU 48 of the display device 5 and displayed on the LCD 42. Therefore, there is an advantage that, for example, an image of the same inspection target inspected in the past and a present image can be compared.

Third Embodiment

An endoscope system according to a third embodiment of the present invention is explained. In the following explanation, components same as those of the endoscope system 1 according to the first embodiment explained above are denoted by the same reference numerals and signs and specific explanation of the components is omitted.

Figure 22:
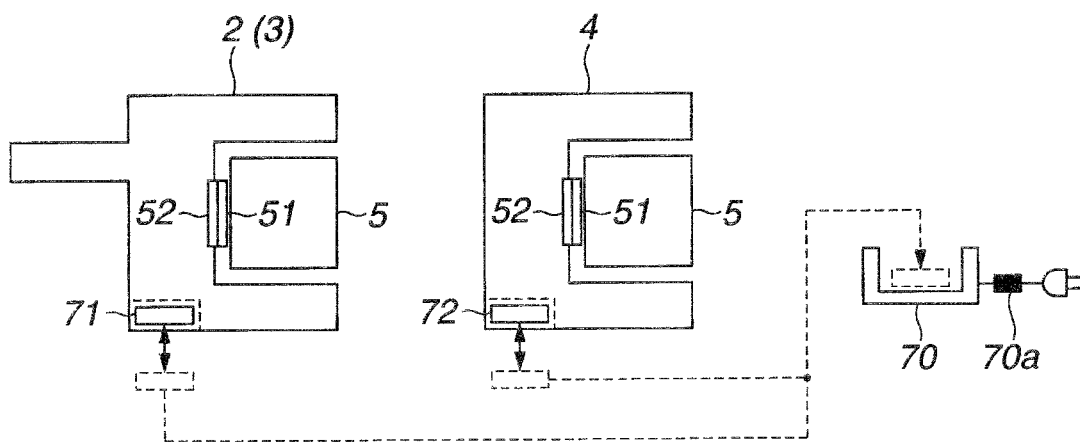
FIG. 22 is a diagram showing the configurations of a flexible endoscope apparatus and a rigid endoscope apparatus including a detachable battery, a display device, and a battery holder according to a third embodiment.
Figure 23:
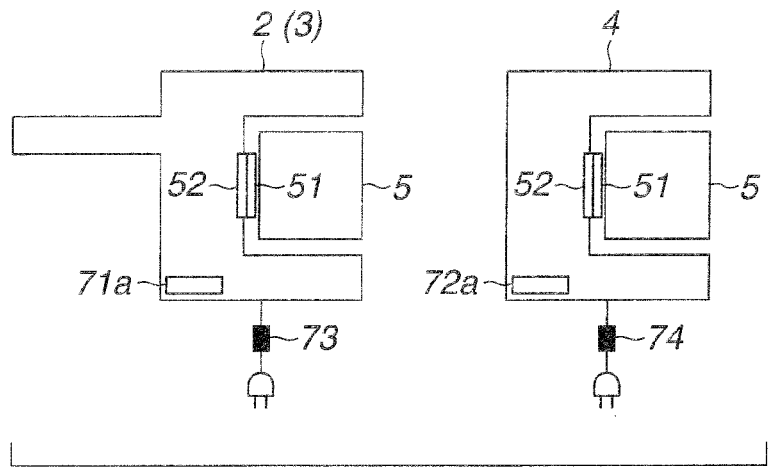
FIG. 23 is a diagram showing the configurations of the flexible endoscope apparatus and the rigid endoscope apparatus of a battery built-in type to which an AC adapter is connected and the display device according to the third embodiment.
Figure 24:
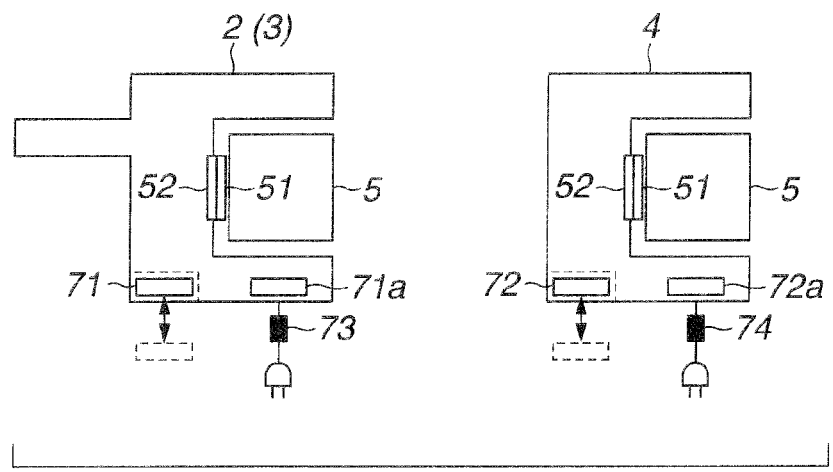
FIG. 24 is a diagram showing the configurations of the flexible endoscope apparatus and the rigid endoscope apparatus of the battery built-in type that include detachable primary batteries and to which the AC adapter is connected and the display device according to the third embodiment.
Figure 25:
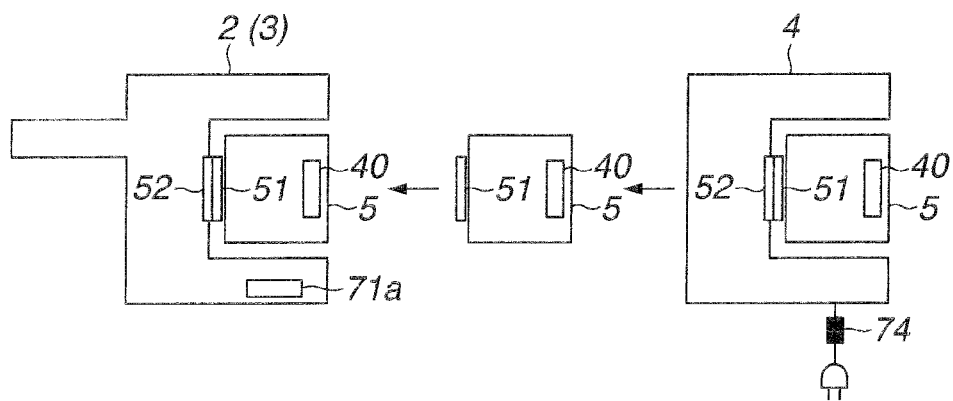
FIG. 25 is a diagram showing the configurations of the flexible endoscope apparatus and the rigid endoscope apparatus of the battery built-in type, a monitor holder to which the AC adapter is connected, and the display device according to the third embodiment.
Figure 26:
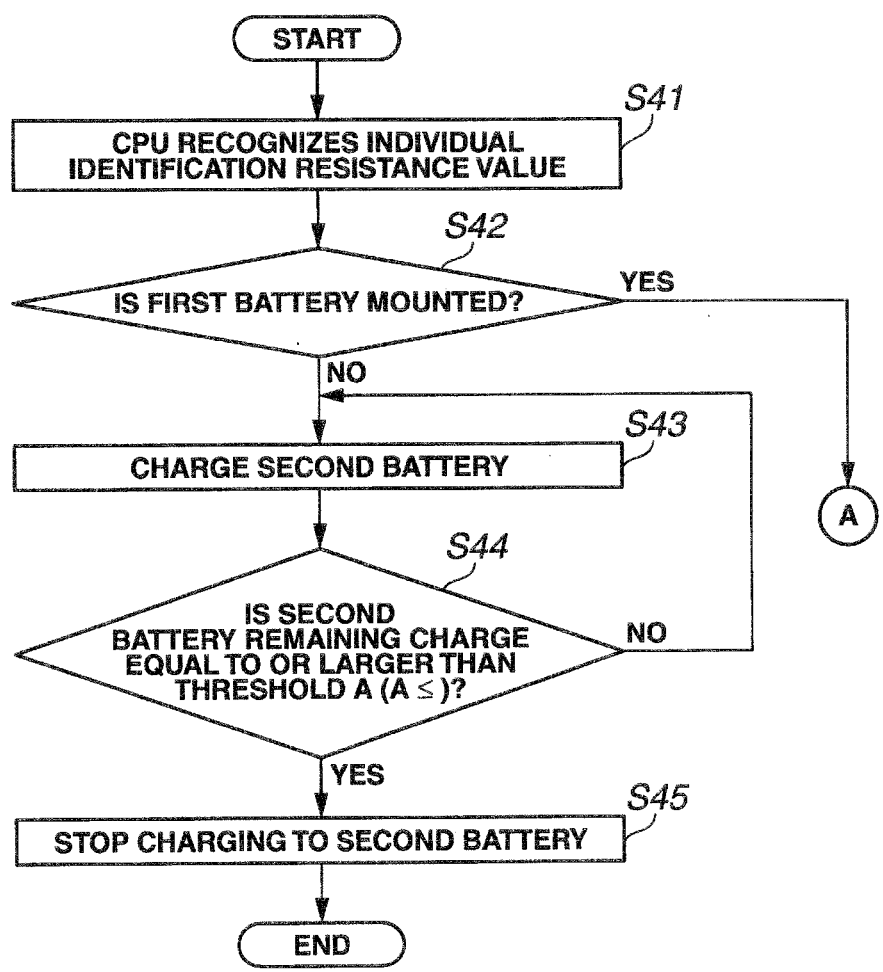
FIG. 26 is a flowchart corresponding to FIG. 24 and for explaining a control example for charging a battery carried out by a control section of the display device when the display device is placed on the flexible endoscope apparatus or the rigid endoscope apparatus.
Figure 27:
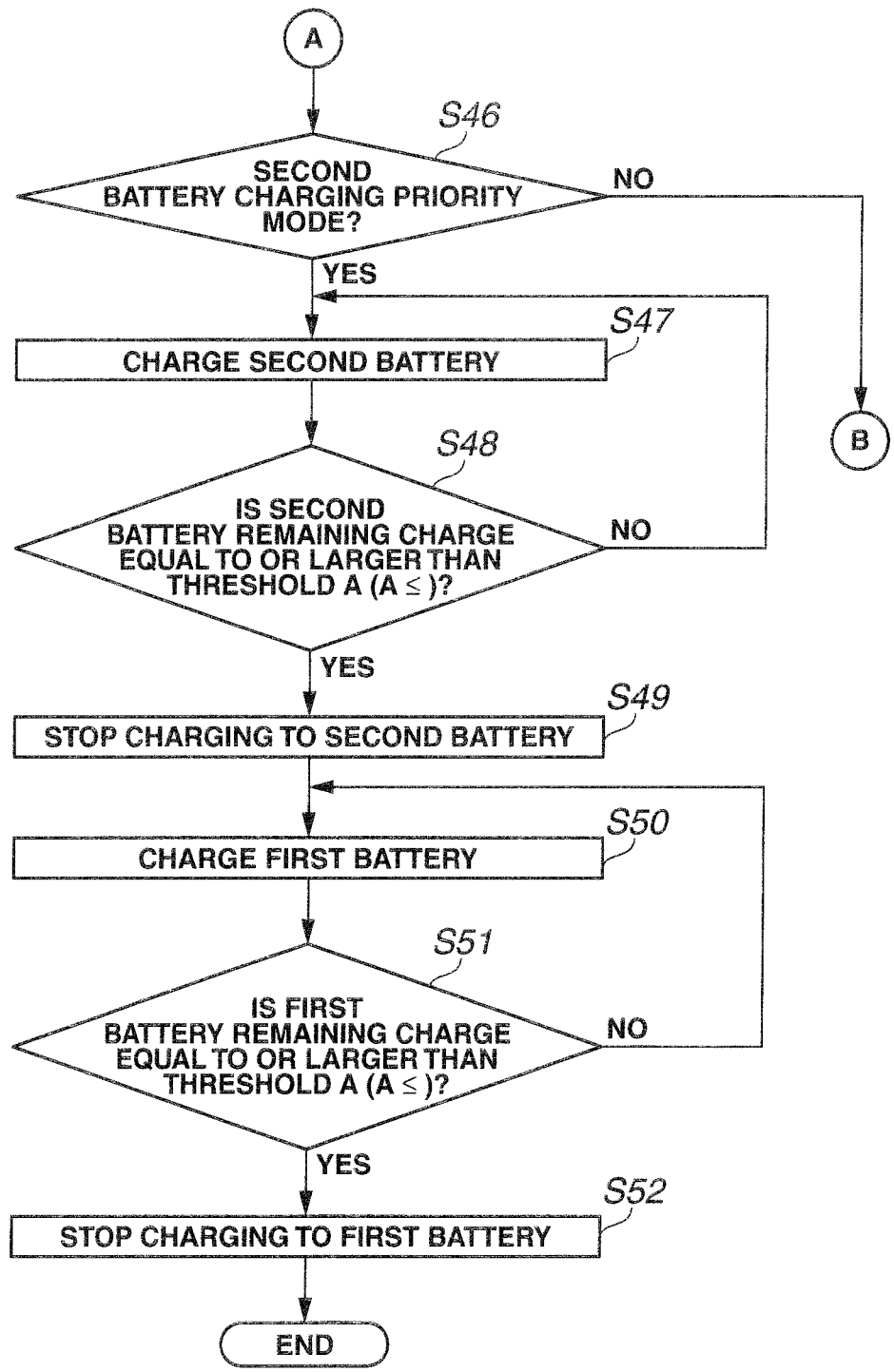
FIG. 27 is a flowchart of processing following FIG. 26 for explaining the control example for charging the battery carried out by the control section of the display device when the display device is placed on the flexible endoscope apparatus or the rigid endoscope apparatus.
Figure 28:
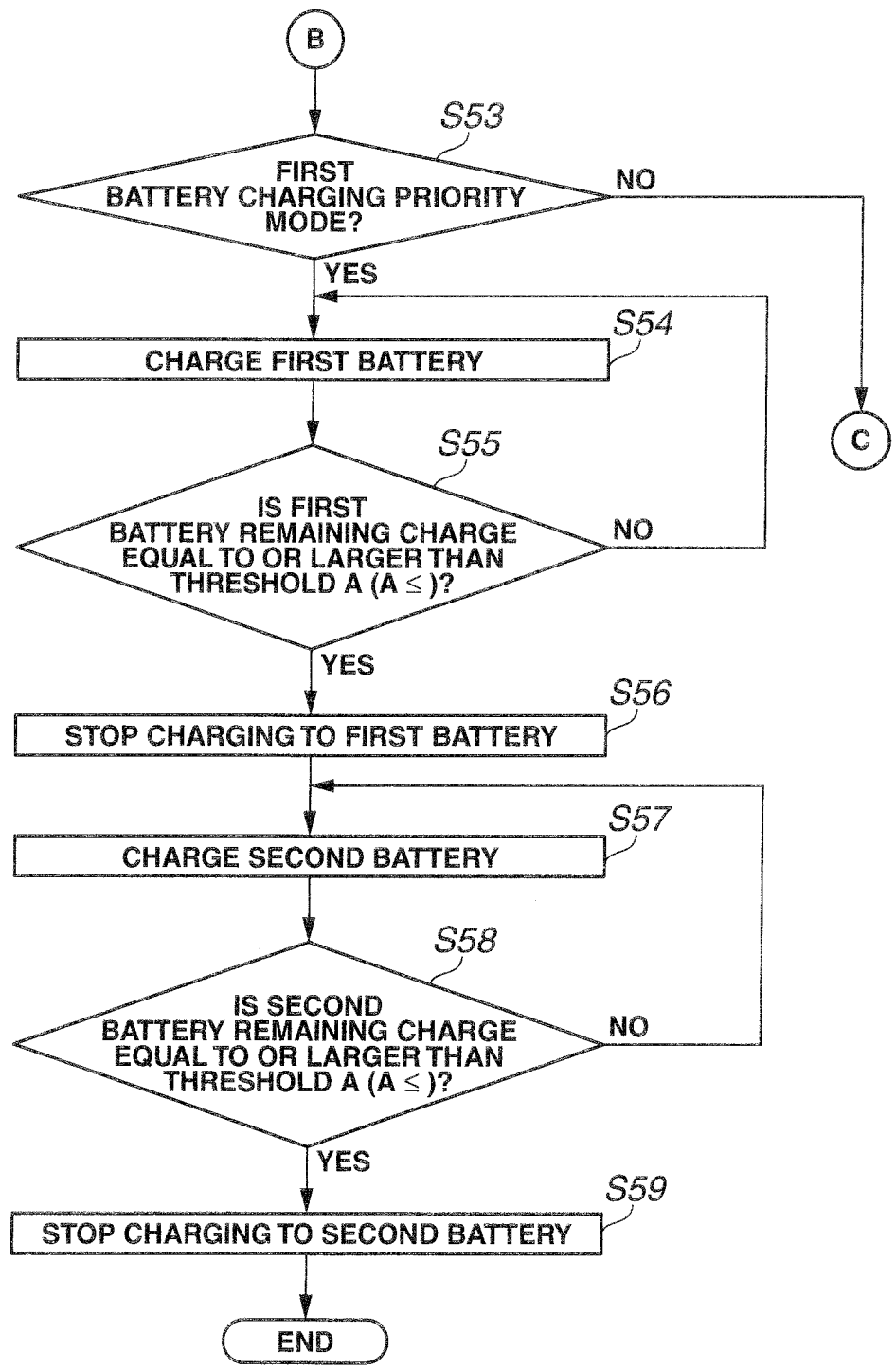
FIG. 28 is a flowchart of processing following FIG. 27 for explaining the control example for charging the battery carried out by the control section of the display device when the display device is placed on the flexible endoscope apparatus or the rigid endoscope apparatus.
Figure 29:
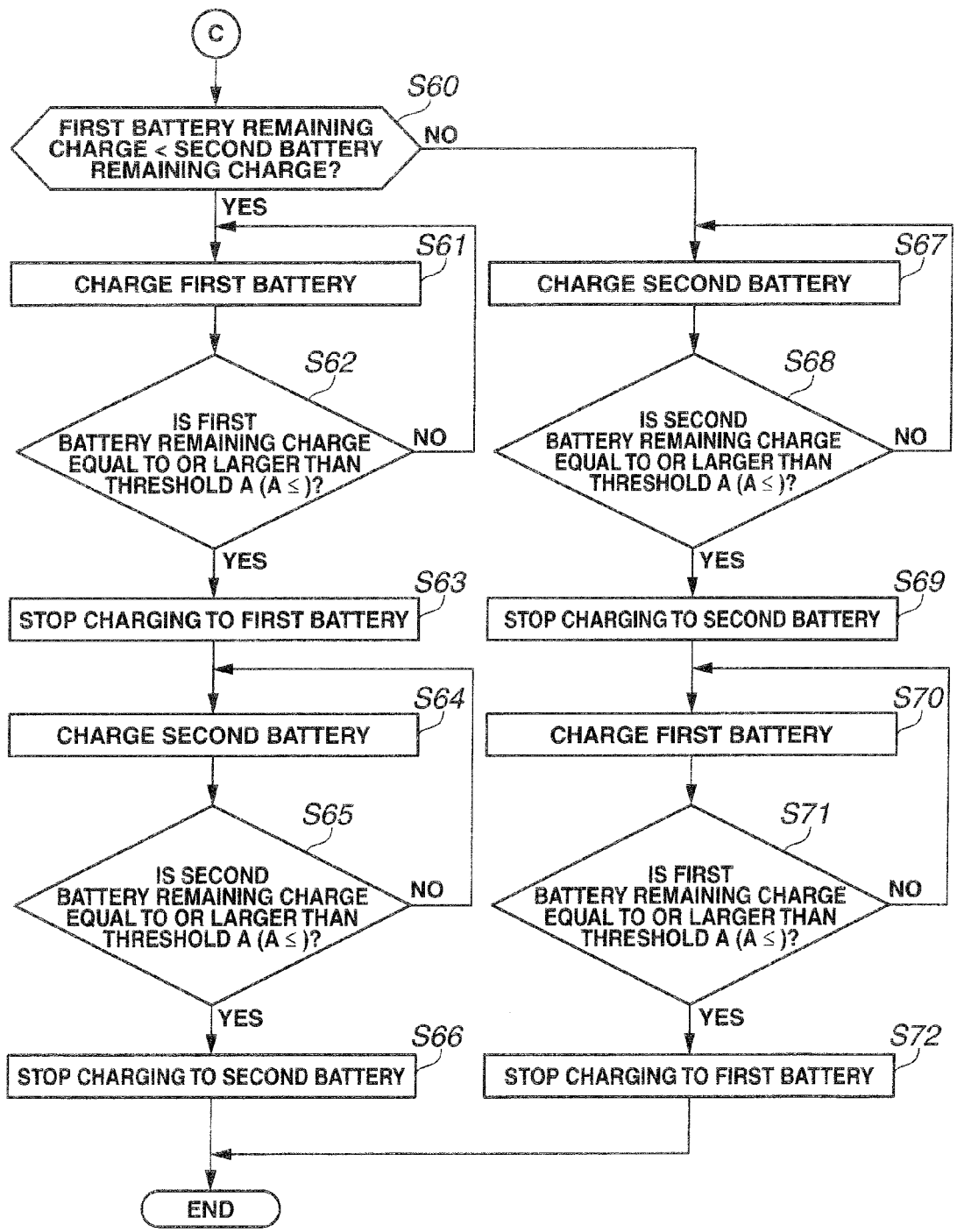
FIG. 29 is a flowchart of processing following FIG. 28 for explaining the control example for charging the battery carried out by the control section of the display device when the display device is placed on the flexible endoscope apparatus or the rigid endoscope apparatus.
Figure 30:
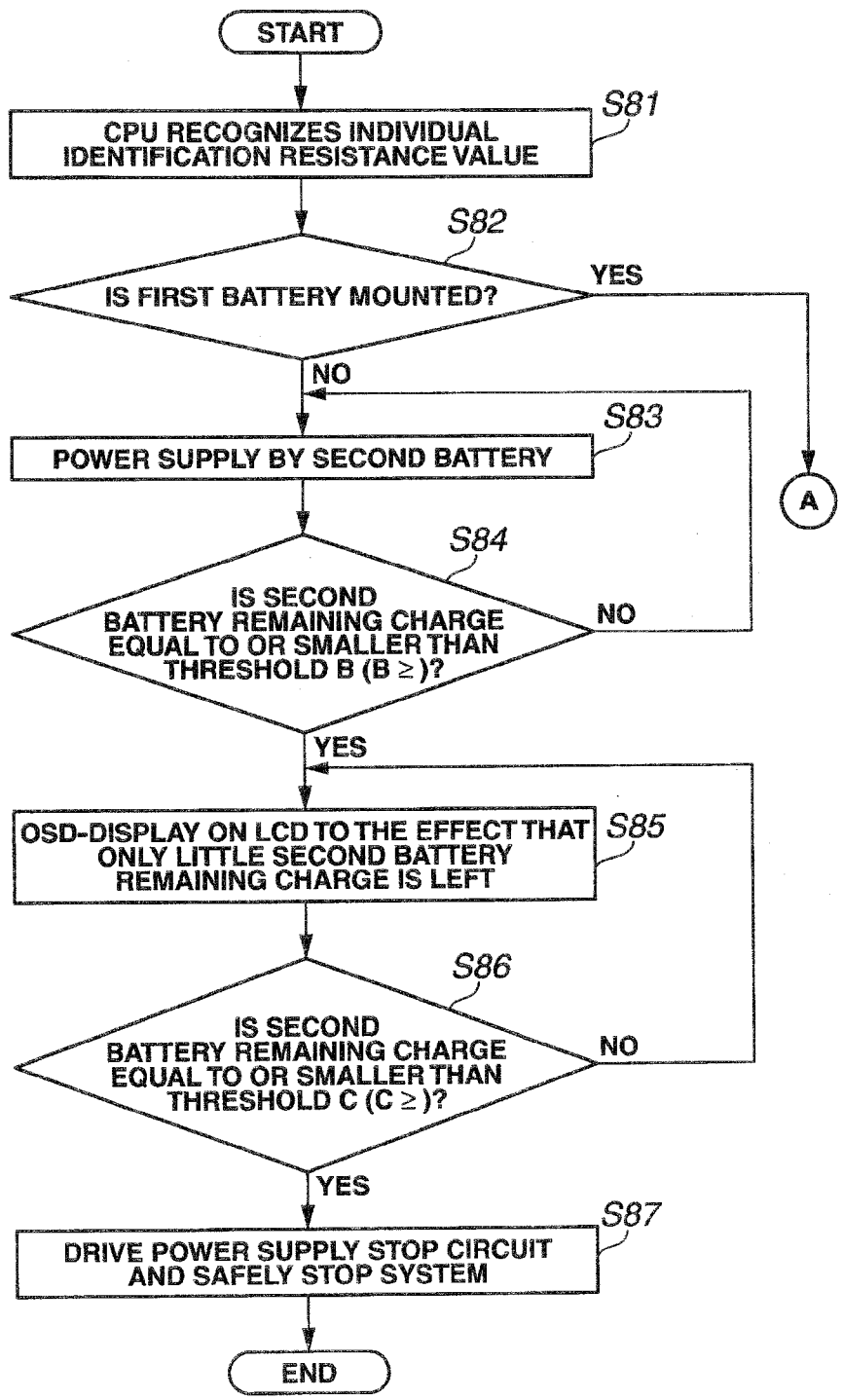
FIG. 30 is a flowchart for explaining a control example for charging a battery carried out by a control section of a display device when the display device is placed on a flexible endoscope apparatus or a rigid endoscope apparatus according to a first modification.
Figure 31:
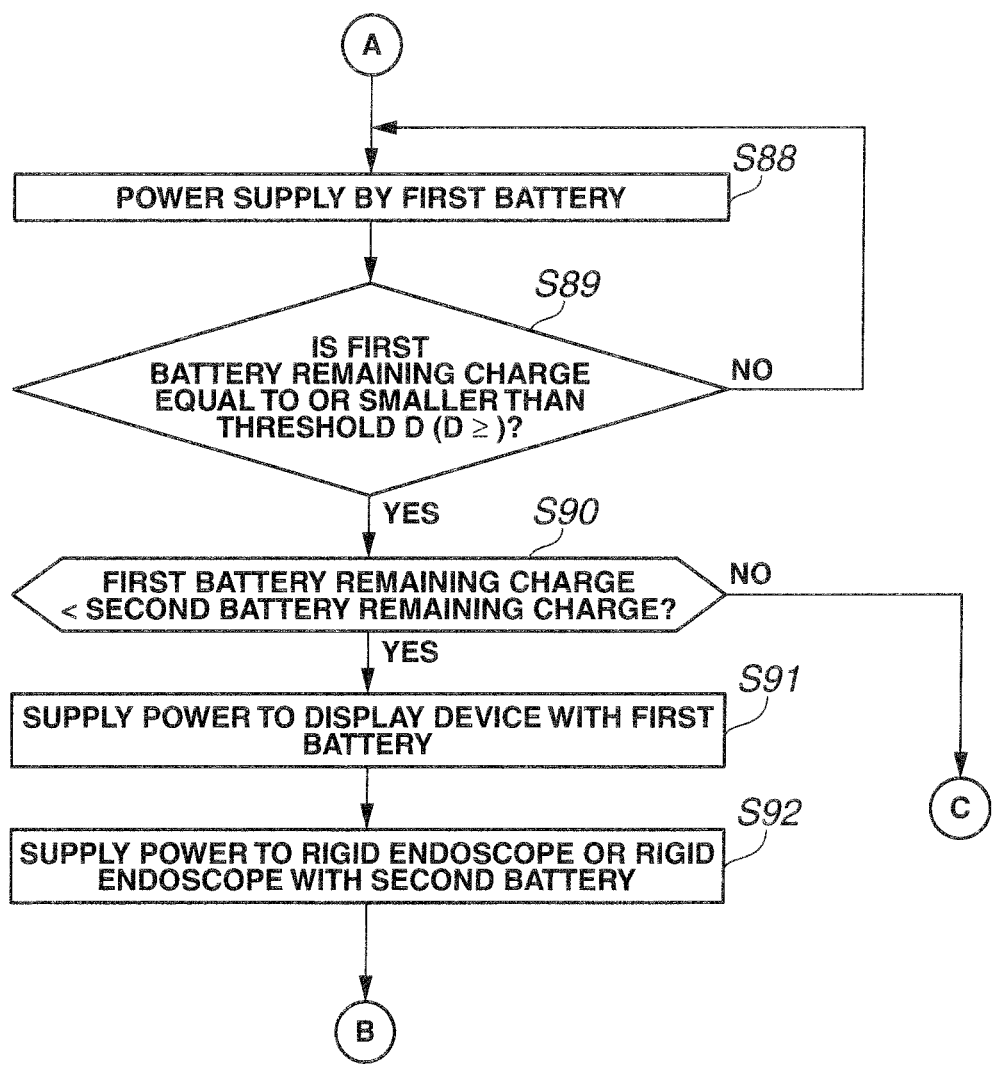
FIG. 31 is a flowchart of processing following FIG. 30 for explaining the control example for charging the battery carried out by the control section of the display device when the display device is placed on the flexible endoscope apparatus or the rigid endoscope apparatus.
Figure 32:
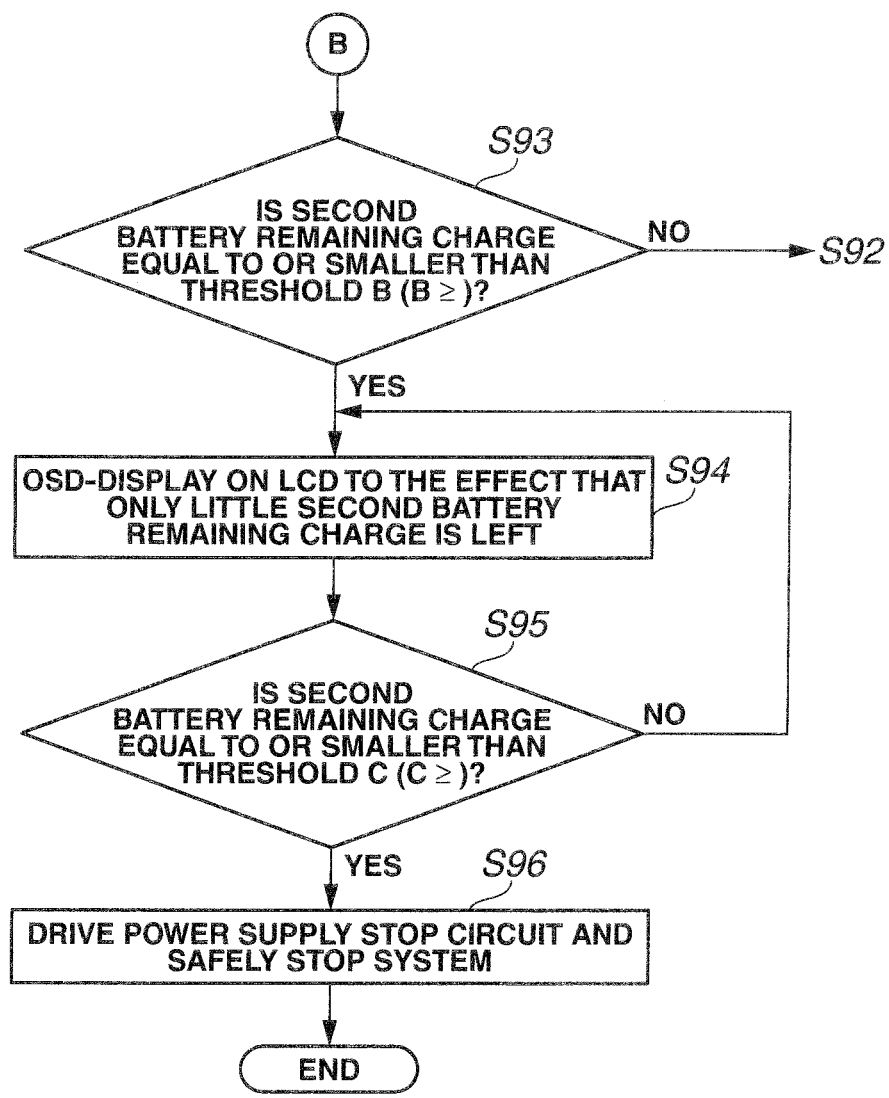
FIG. 32 is a flowchart of processing following FIG. 31 for explaining the control example for charging the battery carried out by the control section of the display device when the display device is placed on the flexible endoscope apparatus or the rigid endoscope apparatus.
Figure 33:
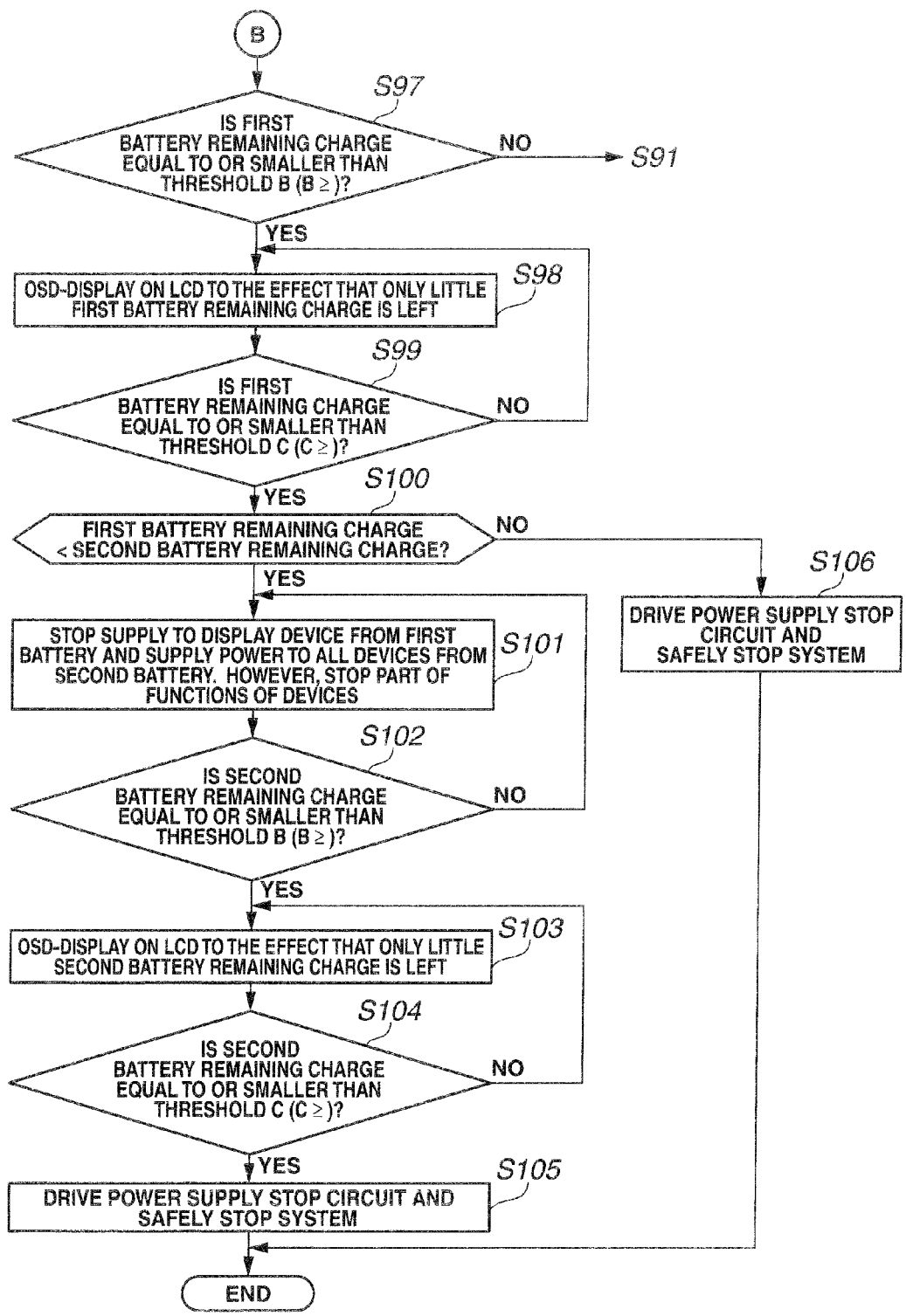
FIG. 33 is a flowchart for explaining a control example for charging a battery carried out by a control section of a display device when the display device is placed on a flexible endoscope apparatus or a rigid endoscope apparatus according to a second modification.
Figure 34:
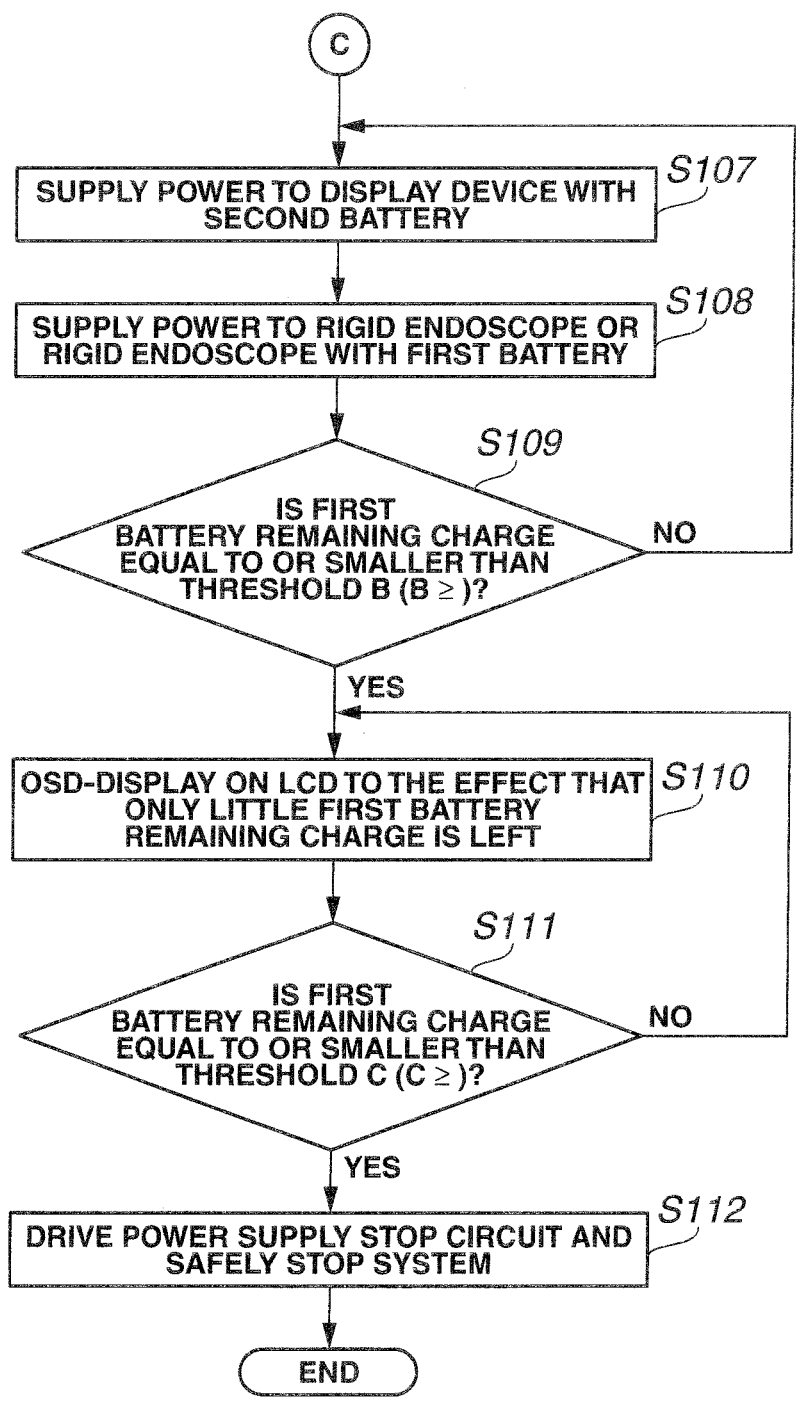
FIG. 34 is a flowchart of processing following FIG. 31 for explaining the control example for charging the battery carried out by the control section of the display device when the display device is placed on the flexible endoscope apparatus or the rigid endoscope apparatus.
Figure 35:
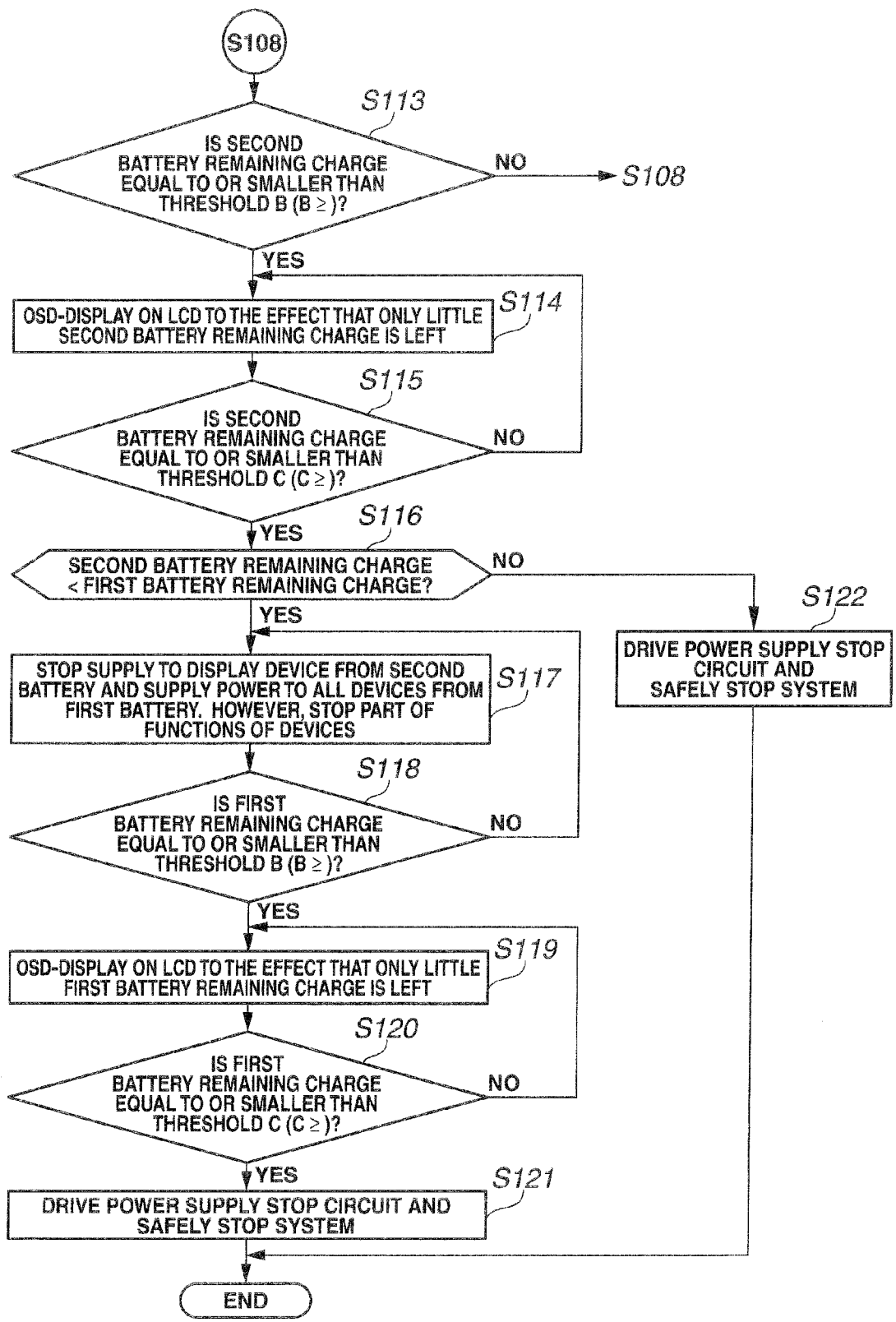
FIG. 35 is a flowchart for explaining a control example for charging a battery carried out by a control section of a display device when the display device is placed on a flexible endoscope apparatus or a rigid endoscope apparatus according to a third modification.
Figure 36:
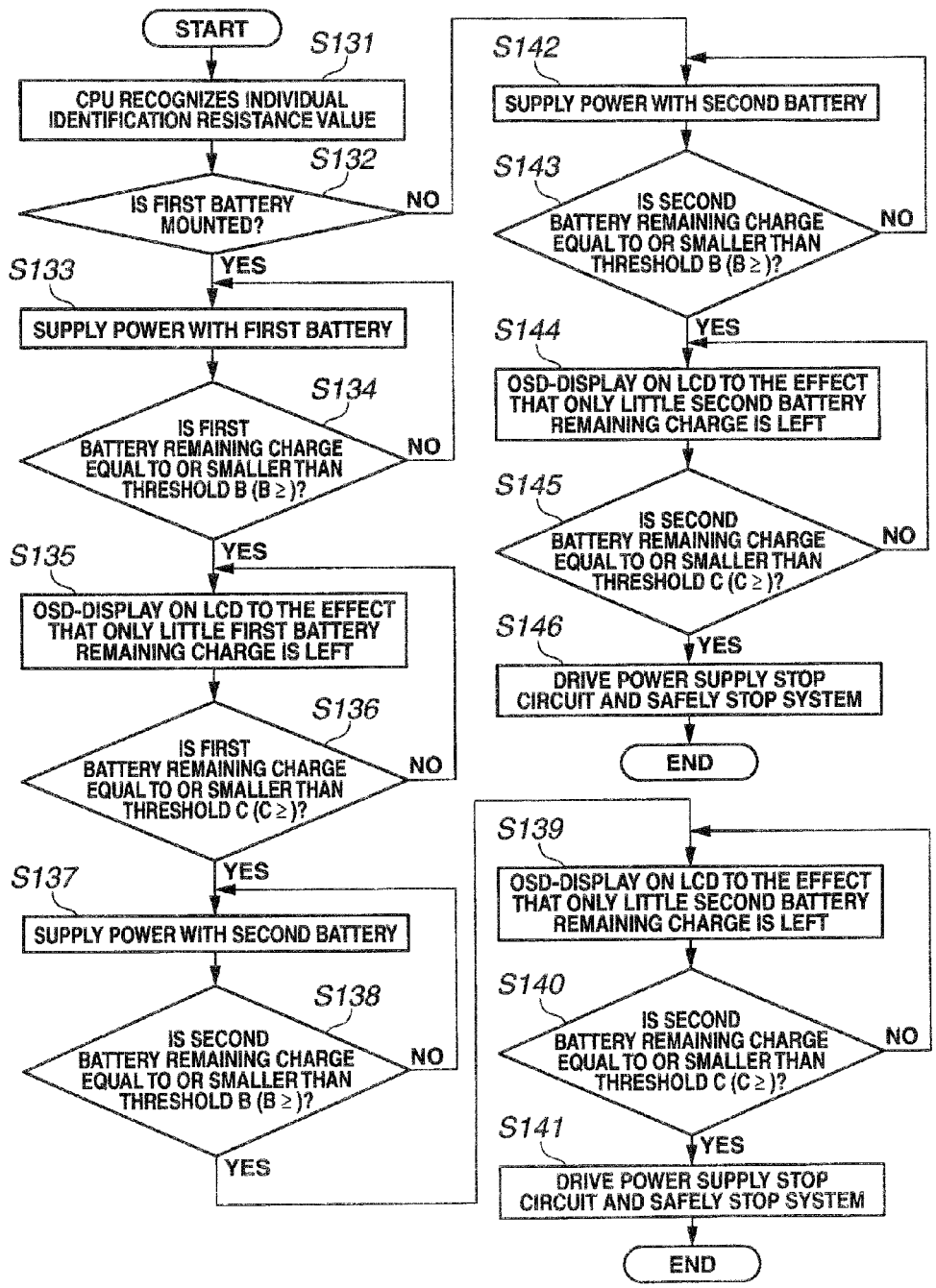
FIG. 36 is a flowchart for explaining a control example for charging a battery carried out by a control section of a display device when the display device is placed on a flexible endoscope apparatus or a rigid endoscope apparatus according to a fourth modification.
Figure 37:
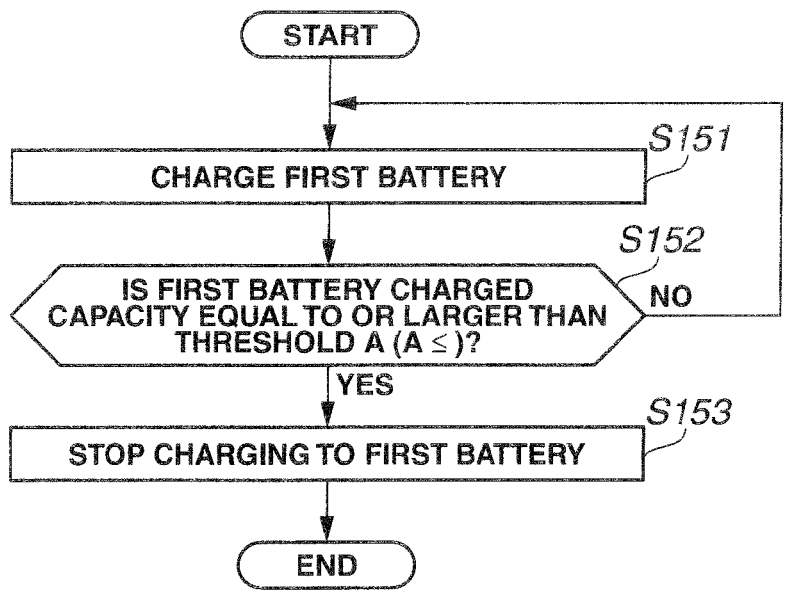
FIG. 37 is a flowchart corresponding to FIG. 25 and for explaining a control example for charging the battery carried out by the control section of the display device when the display device is placed on the monitor holder.
Figure 38:
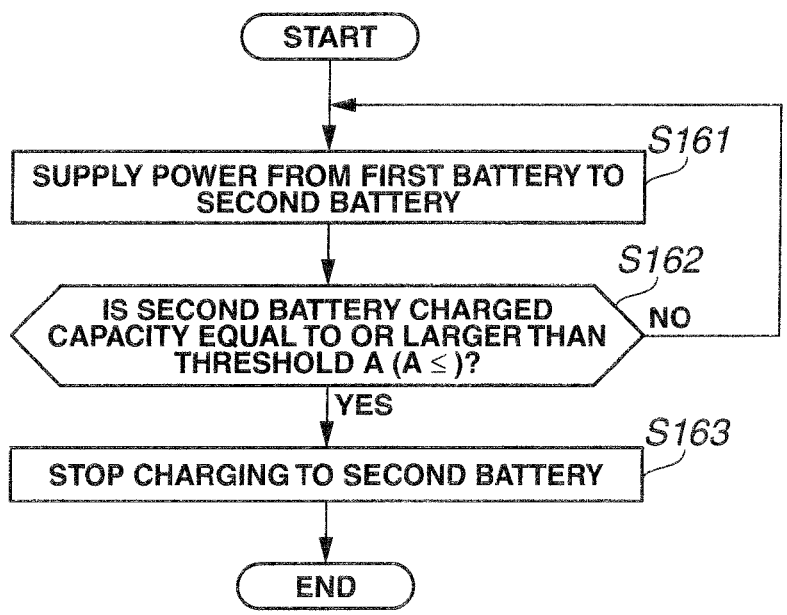
FIG. 38 is a flowchart corresponding to FIG. 25 and for explaining a control example for charging the battery carried out by the control section of the display device when the display device is placed on the flexible endoscope apparatus or the rigid endoscope apparatus.

FIGS. 22 to 38 relate to the third embodiment of the present invention. FIG. 22 is a diagram showing the configurations of a flexible endoscope apparatus and a rigid endoscope apparatus including a detachable battery, a display device, and a battery holder, FIG. 23 is a diagram showing the configurations of the flexible endoscope apparatus and the rigid endoscope apparatus of a battery built-in type to which an AC adapter is connected and the display device, FIG. 24 is a diagram showing the configurations of the flexible endoscope apparatus and the rigid endoscope apparatus of the battery built-in type that include detachable primary batteries and to which the AC adapter is connected and the display device, FIG. 25 is a diagram showing the configurations of the flexible endoscope apparatus and the rigid endoscope apparatus of the battery built-in type, a monitor holder to which the AC adapter is connected, and the display device 5, FIG. 26 is a flowchart corresponding to FIG. 24 and for explaining a control example for charging a battery carried out by a control section of the display device when the display device is placed on the flexible endoscope apparatus or the rigid endoscope apparatus, FIG. 27 is a flowchart of processing following FIG. 26 for explaining the control example for charging the battery carried out by the control section of the display device when the display device is placed on the flexible endoscope apparatus or the rigid endoscope apparatus, FIG. 28 is a flowchart of processing following FIG. 27 for explaining the control example for charging the battery carried out by the control section of the display device when the display device is placed on the flexible endoscope apparatus or the rigid endoscope apparatus, FIG. 29 is a flowchart of processing following FIG. 28 for explaining the control example for charging the battery carried out by the control section of the display device when the display device is placed on the flexible endoscope apparatus or the rigid endoscope apparatus, FIG. 30 is a flowchart for explaining a control example for charging a battery carried out by a control section of a display device when the display device is placed on a flexible endoscope apparatus or a rigid endoscope apparatus according to a first modification, FIG. 31 is a flowchart of processing following FIG. 30 for explaining the control example for charging the battery carried out by the control section of the display device when the display device is placed on the flexible endoscope apparatus or the rigid endoscope apparatus, FIG. 32 is a flowchart of processing following FIG. 31 for explaining the control example for charging the battery carried out by the control section of the display device when the display device is placed on the flexible endoscope apparatus or the rigid endoscope apparatus, FIG. 33 is a flowchart for explaining a control example for charging a battery carried out by a control section of a display device when the display device is placed on a flexible endoscope apparatus or a rigid endoscope apparatus according to a second modification, FIG. 34 is a flowchart of processing following FIG. 31 for explaining the control example for charging the battery carried out by the control section of the display device when the display device is placed on the flexible endoscope apparatus or the rigid endoscope apparatus, FIG. 35 is a flowchart for explaining a control example for charging a battery carried out by a control section of a display device when the display device is placed on a flexible endoscope apparatus or a rigid endoscope apparatus according to a third modification, FIG. 36 is a flowchart for explaining a control example for charging a battery carried out by a control section of a display device when the display device is placed on a flexible endoscope apparatus or a rigid endoscope apparatus according to a fourth modification, FIG. 37 is a flowchart corresponding to FIG. 25 and for explaining a control example for charging the battery carried out by the control section of the display device when the display device is placed on the monitor holder, and FIG. 38 is a flowchart corresponding to FIG. 25 and for explaining a control example for charging the battery carried out by the control section of the display device when the display device is placed on the flexible endoscope apparatus or the rigid endoscope apparatus.

In this embodiment, various configurations in which a battery for power supply is provided in the flexible endoscope 2, the rigid endoscope 3, or the monitor holder 4 besides the display device 5 are explained.

First, as shown in FIG. 22, the flexible endoscope 2 and the rigid endoscope 3 include detachable batteries 71 and the monitor holder 4 also includes a detachable battery 72.

These batteries 71 and 72 are chargeable by a common battery charger 70. This battery charger 70 is connected to a detachable AC adapter 70a for power supply.

By providing the batteries 71 and 72 for power supply in the flexible endoscope 2, the rigid endoscope 3, and the monitor holder 4 in this way, a storage capacity of the entire system can be increased in addition to the battery 40 of the display device 5 (see FIG. 9, etc.). Therefore, it is possible to perform use (inspection) for a long time.

As shown in FIG. 23, the flexible endoscope 2 and the rigid endoscope 3 may include batteries 71a of a built-in type and the monitor holder 4 may also include a battery 72a of the built-in type. An AC adapter 73 for power supply is connectable to the flexible endoscope 2 and the rigid endoscope 3. An AC adapter 74 for power supply is also connectable to the monitor holder 4. A battery charging function (not shown) is incorporated in the flexible endoscope 2, the rigid endoscope 3, and the monitor holder 4 by power supply from the AC adapters 73 and 74 connected to a power supply.

With such a configuration, as in the above description, the use (inspection) of the entire system can be performed for a long time and, in addition, the battery charger 70 is unnecessary. Moreover, when a commercial power supply can be used in a place of an inspection, the flexible endoscope 2, the rigid endoscope 3, and the monitor holder 4 can be driven by power supply via the AC adapters 73 and 74.

Further, as shown in FIG. 24, the flexible endoscope 2, the rigid endoscope 3, and the monitor holder 4 may include all of the detachable batteries 71 and 72 shown in FIG. 22, the batteries 71a and 72a of the built-in type shown in FIG. 23, and the detachable AC adapters 73 and 74. By adopting such a configuration, even if the detachable batteries 71 and 72 cause flat battery, the flexible endoscope 2, the rigid endoscope 3, and the monitor holder 4 can be driven by the batteries 71a and 72a of the built-in type while the batteries 71 and 72 are charged. Therefore, it is unnecessary to suspend an inspection and it is possible to continuously perform the inspection.

As shown in FIG. 25, the flexible endoscope 2 and the rigid endoscope 3 may include the batteries 71a of the built-in type. The batteries 71a of the built-in type may be charged from the battery 40 of the display device 5. In other words, the battery 40 of the display device 5 is charged when the display device 5 is placed on the monitor holder 4.

As such a configuration, for example, when the flexible endoscope 2 or the rigid endoscope 3 is used under an explosive atmosphere, a configuration in which an electric contact of the flexible endoscope 2 or the rigid endoscope 3 is exposed to an outside is undesirable. In other words, for example, in the flexible endoscope 2 or the rigid endoscope 3, a configuration in which a plug to which an AC adapter is connected is exposed is undesirable. When the AC adapter is used, there is a limitation that the flexible endoscope 2 or the rigid endoscope 3 has to be formed in an explosion proof structure. Therefore, it is preferable to adopt a configuration for preventing power supply by the AC adapter during an inspection as shown in FIG. 25. Therefore, when the display device 5 is placed on the flexible endoscope 2 or the rigid endoscope 3, the battery 71a in the flexible endoscope 2 or the rigid endoscope 3 is charged from the sufficiently-charged battery 40 in the display device 5.

A control example for charging the detachable battery 71 and the battery 71a of the built-in type carried out by the CPU 48 of the display device 5 according to processing shown in flowcharts of FIGS. 26 to 29 when the display device 5 is placed on the flexible endoscope 2 or the rigid endoscope 3 as shown in FIG. 24 is explained below.

In the following explanation, the battery 71a of the built-in type is represented as first battery 71a and the detachable battery 71 is represented as second battery 71. The flexible endoscope 2 or the rigid endoscope 3 is in a state in which the AC adapters 73 and 74 are connected to a commercial power supply.

First, when the display device 5 is placed on the flexible endoscope 2 or the rigid endoscope 3, the CPU 48 of the display device 5 recognizes a resistance value of the individual identification resistor 64 of the connected apparatus via the connector sections 51 and 52 (S41). The CPU 48 determines whether the first battery 71a is mounted on the connected flexible endoscope 2 or rigid endoscope 3 (S42).

When the first battery 71a is not mounted on the flexible endoscope 2 or the rigid endoscope 3, the CPU 48 controls to charge the second battery 71 (S43). The CPU 48 determines whether remaining charge of the second battery 71 is equal to or larger than a predetermined threshold A (S44). The CPU 48 performs processing for returning to step S43 until the remaining charge of the second battery 71 increases to be equal to or larger than the predetermined threshold A.

When the remaining charge of the second battery 71 increases to be equal to or larger than the predetermined threshold A, the CPU 48 stops the charging control of the second battery 71 (S45) and ends all the processing.

When the CPU 48 determines in the processing in step S42 that the first battery 71a is mounted on the flexible endoscope 2 or the rigid endoscope 3, as shown in FIG. 27, the CPU 48 determines whether a second battery charging priority mode is selected (set) (S46). The user can set this second battery charging priority mode by operating either one of the plural operation switches 43 and 44 (see FIGS. 1 to 4).

When the CPU 48 determines in the processing in step S42 that the second battery charging priority mode is set, the CPU 48 controls to charge the second battery 71 (S47). The CPU 48 determines whether the remaining charge of the second battery 71 is equal to or larger than the predetermined threshold A (S48), The CPU 48 repeatedly performs processing for returning to step S47 until the remaining charge of the second battery 71 increases to be equal to or larger than the predetermined threshold A.

When the remaining charge of the second battery 71 increases to be equal to or larger than the predetermined threshold A, the CPU 48 stops the charging control of the second battery 71 (S49). Subsequently, the CPU 48 controls to charge the first battery 71a (S50), The CPU 48 determines whether remaining charge of the first battery 71a is equal to or larger than the predetermined threshold A (S51). The CPU 48 repeatedly performs processing for returning to step S50 until the remaining charge of the first battery 71a increases to be equal to or larger than the predetermined threshold A.

When the remaining charge of the first battery 71a increases to be equal to or larger than the predetermined threshold A, the CPU 48 stops the charging control of the first battery 71a (S52) and ends all the processing. When the CPU 48 determines in the processing in step S46 that the second battery charging priority mode is not selected (set), as shown in FIG. 28, the CPU 48 determines whether a first battery charging priority mode is set (S46). The user can set the first battery charging priority mode as well by operating either one of the plural operation switches 43 and 44 (see FIGS. 1 to 4).

The CPU 48 determines in the processing in step S53 that the first battery charging priority mode is set, the CPU 48 controls to charge the first battery 71a (S54). The CPU 48 determines whether the remaining charge of the first battery 71a is equal to or larger than the predetermined threshold A (S55). The CPU 48 repeatedly performs processing for returning to step S54 until the remaining charge of the first battery 71a increases to be equal to or larger than the predetermined threshold A.

When the remaining charge of the first battery 71a increases to be equal to or larger than the predetermined threshold A, the CPU 48 stops the charging control of the first battery 71a (S56). Subsequently, the CPU 48 controls to charge the second battery 71 (S57). The CPU 48 determines whether the remaining charge of the second battery 71 is equal to or larger than the predetermined threshold A (S58). The CPU 48 repeatedly performs processing for returning to step S57 until the remaining charge of the second battery 71 increases to be equal to or larger than the predetermined threshold A. When the remaining charge of the second battery 71 increases to be equal to or larger than the predetermined threshold A, the CPU 48 stops the charging control of the second battery 71 (S52) and ends all the processing.

When the CPU 48 determines in the processing in step S53 that a battery remaining amount priority mode is selected (set), as shown in FIG. 29, the CPU 48 determines whether a remaining amount of the first battery 71a is smaller than a remaining amount of the second battery 71 (S60). The user can set this battery remaining amount priority mode as well by operating either one of the plural operation switches 43 and 44 (see FIGS. 1 to 4).

When the CPU 48 determines in the processing in step S60 that the remaining amount of the first battery 71a is smaller than the remaining amount of the second battery 71, the CPU 48 controls to charge the first battery 71a (S61). The CPU 48 determines whether the remaining charge of the first battery 71a is equal to or larger than the predetermined threshold A (S62). The CPU 48 repeatedly performs processing for returning to step S61 until the remaining charge of the first battery 71a increases to be equal to or larger than the predetermined threshold A.

When the remaining charge of the first battery 71a increases to be equal to or larger than the predetermined threshold A, the CPU 48 stops the charging control of the first battery 71a (S63). Subsequently, the CPU 48 controls to charge the second battery 71 (S64). The CPU 48 determines whether the remaining charge of the second battery 71 is equal to or larger than the predetermined threshold A (S65). The CPU 48 repeatedly performs processing for returning to step S64 until the remaining charge of the second battery 71 increases to be equal to or larger than the predetermined threshold A. When the remaining charge of the second battery 71 increases to be equal to or larger than the predetermined threshold A, the CPU 48 stops the charging control of the second battery 71 (S66) and ends the processing.

When the CPU 48 determines in the processing in step S60 that the remaining amount of the first battery 71a is larger than the remaining amount of the second battery 71, i.e., the remaining amount of the second battery 71 is smaller than the remaining amount of the first battery 71a, the CPU 48 controls to charge the second battery 71 (S67). The CPU 48 determines whether the remaining charge of the second battery 71 is equal to or larger than the predetermined threshold A (S68). The CPU 48 repeatedly performs processing for returning to step S67 until the charging amount of the second battery 71 increases to be equal to or larger than the predetermined threshold A.

When the remaining charge of the second battery 71 increases to be equal to or larger than the predetermined threshold A, the CPU 48 stops the charging control of the second battery 71 (S69). Subsequently, the CPU 48 controls to charge the first battery 71a (S70). The CPU 48 determines whether the remaining charge of the first battery 71a is equal to or larger than the predetermined threshold A (S71). The CPU 48 repeatedly performs processing for returning to step S50 until the remaining charge of the first battery 71a increases to be equal to or larger than the predetermined threshold A. When the remaining charge of the first battery 71a increases to be equal to or larger than the predetermined threshold A, the CPU 48 stops the charging control of the first battery 71a (S72) and ends all the processing.

As explained above, according to such a control example by the CPU 48, as the charging control of the batteries 71 and 71a, the user can select (set) the three modes: the first battery charging priority mode, the second battery charging priority mode, and the battery remaining amount priority mode.

In a state in which the AC adapters 73 and 74 are not connected to the commercial power supply, when the display device 5 is placed on the flexible endoscope 2 or the rigid endoscope 3 as shown in FIG. 24, the control example for charging the detachable battery 71 and the battery 71a of the built-in type carried out by the CPU 48 of the display device 5 is executed according to the processing shown in the flowcharts of FIGS. 30 to 36.

First, when the display device 5 is placed on the flexible endoscope 2 or the rigid endoscope 3, the CPU 48 of the display device 5 recognizes a resistance value of the individual identification resistor 64 of the connected apparatus via the connector sections 51 and 52 (S81). The CPU 48 determines whether the first battery 71a is mounted on the connected flexible endoscope 2 or rigid endoscope 3 (S82).

When the first battery 71a is not mounted on the flexible endoscope 2 or the rigid endoscope 3, the CPU 48 controls to supply, with the second battery 71, power to the display device 5 and the flexible endoscope 2 or the rigid endoscope 3 on which this display device 5 is mounted (S83), The CPU 48 determines whether remaining charge of the second battery 71 is equal to or smaller than a predetermined threshold B (S84). The CPU 48 repeatedly performs processing for returning to step S83 until the remaining charge of the second battery 71 decreases to be equal to or smaller than the predetermined threshold B.

When the remaining charge of the second battery 71 decreases to be equal to or smaller than the predetermined threshold B, the CPU 48 OSD (on screen display)-displays, on the LCD 42 of the display device 5, a warning to the effect that only a little remaining amount of the second battery 71 is left (S85).

Thereafter, the CPU 48 determines whether the remaining charge of the second battery 71 is equal to or smaller than a predetermined threshold C (S86). This threshold C of remaining charge is a value smaller than the threshold B of remaining charge (B>C). The CPU 48 repeatedly performs processing for returning to step S85 until the remaining charge of the second battery 71 decreases to be equal to or smaller than the predetermined threshold C.

When the remaining charge of the second battery 71 decreases to be equal to or smaller than the predetermined threshold C, the CPU 48 controls to drive a power supply stop circuit (not shown) to safely stop the system (S87) and ends all the processing.

When the CPU 48 determines in the processing in step S42 that the first battery 71*a* is mounted on the flexible endoscope 2 or the rigid endoscope 3, as shown in FIG. 31, the CPU 48 controls to supply, with the first battery 71*a*, power to the display device 5 and the flexible endoscope 2 or the rigid endoscope 3 on which this display device 5 is mounted (S88). The CPU 48 determines whether the remaining charge of the first battery 71*a* is equal to or smaller than a predetermined threshold D (S89). The threshold D of remaining charge is a value smaller than the threshold B of remaining charge and larger than the threshold C of remaining charge. In other words, a relation among the thresholds B, C, and D is B>D>C, The CPU 48 repeatedly performs processing for returning to step S88 until the remaining charge of the first battery 71*a* decreases to be equal to or smaller than the predetermined threshold D.

When the remaining charge of the first battery 71*a* decreases to be equal to or smaller than the predetermined threshold D, the CPU 48 determines whether the remaining amount of the first battery 71*a* is smaller than the remaining amount of the second battery 71 (S90).

When the CPU 48 determines in the processing in step S90 that the remaining amount of the first battery 71*a* is smaller than the remaining amount of the second battery 71, the CPU 48 controls to supply driving power by the first battery 71*a* only to the display device 5 (S91). The CPU 48 controls to supply driving power by the second battery 71 to the flexible endoscope 2 or the rigid endoscope 3 on which the display device 5 is mounted (S92).

Subsequently, as shown in FIG. 32, the CPU 48 determines whether the remaining charge of the second battery 71 is equal to or smaller than the predetermined threshold B (S93). The CPU 48 repeatedly performs processing for returning to step S92 until the remaining charge of the second battery 71 decreases to be equal to or smaller than the predetermined threshold B.

When the remaining charge of the second battery 71 decreases to be equal to or smaller than the predetermined threshold B, the CPU 48 OSD (on screen display)-displays, on the LCD 42 of the display device 5, a warning to the effect that only a little remaining amount of the second battery 71 is left (S94).

Thereafter, the CPU 48 determines whether the remaining charge of the second battery 71 is equal to or smaller than the predetermined threshold C (S95). The CPU 48 performs processing for returning to step S95 until the remaining charge of the second battery 71 decreases to be equal to or smaller than the predetermined threshold C.

When the remaining charge of the second battery 71 decreases to be equal to or smaller than the predetermined threshold C, the CPU 48 controls to drive the power supply stop circuit (not shown) to safely stop the system (S96) and ends all the processing.

After the processing in step S92, the CPU 48 may execute a control example shown in FIG. 33.

Specifically, as shown in FIG. 33, after the processing in step S92, the CPU 48 determines whether the remaining charge of the first battery 71*a* is equal to or smaller than the predetermined threshold B (S97). The CPU 48 repeatedly performs processing for returning to step S91 until the remaining charge of the first battery 71*a* decreases to be equal to or smaller than the predetermined threshold B.

When the remaining charge of the first battery 71*a* decreases to be equal to or smaller than the predetermined threshold B, the CPU 48 OSD (on screen display)-displays, on the LCD 42 of the display device 5, a warning to the effect that only a little remaining amount of the first battery 71*a* is left (S98).

Thereafter, the CPU 48 determines whether the remaining charge of the first battery 71*a* is equal to or smaller than the predetermined threshold C (S99). The CPU 48 performs processing for returning to step S98 until the remaining charge of the first battery 71*a* decreases to be equal to or smaller than the predetermined threshold C.

When the remaining charge of the first battery 71*a* decreases to be equal to or smaller than the predetermined threshold C, the CPU 48 determines whether the remaining amount of the first battery 71*a* is smaller than the remaining amount of the second battery 71 (S100). When the CPU 48 determines that the remaining amount of the first battery 71*a* is smaller than the remaining amount of the second battery 71, the CPU 48 stops the control of the power supply to the display device 5 by the first battery 71*a* and switches the driving power by the second battery 71 to the display device 5 and all the apparatuses, i.e., the flexible endoscope 2 or the rigid endoscope 3 on which this display device 5 is mounted and controls power supply (S101). However, at this point, the CPU 48 performs control for stopping a part of the functions of the flexible endoscope 2 or the rigid endoscope 3.

Subsequently, the CPU 48 determines whether the remaining charge of the second battery 71 is equal to or smaller than the predetermined threshold B (S102). The CPU 48 repeatedly performs processing for returning to step S101 until the remaining charge of the second battery 71 decreases to be equal to or smaller than the predetermined threshold B.

When the remaining charge of the second battery 71 decreases to be equal to or smaller than the predetermined threshold B, the CPU 48 OSD (on screen display)-displays, on the LCD 42 of the display device 5, a warning to the effect that only a little remaining amount of the second battery 71 is left (S103).

Thereafter, the CPU 48 determines whether the remaining charge of the second battery 71 is equal to or smaller than the predetermined threshold C (S104). The CPU 48 repeatedly performs processing for returning to step S103 until the remaining charge of the second battery 71 decreases to be equal to or smaller than the predetermined threshold C.

When the remaining charge of the second battery 71 decreases to be equal to or smaller than the predetermined threshold C, the CPU 48 controls to drive the power supply stop circuit (not shown) to safely stop the system (S105) and ends all the processing.

When the CPU 48 determines in the processing in step S100 that the remaining amount of the first battery 71*a* is larger than the remaining amount of the second battery 71, i.e., the remaining amount of the second battery 71 is smaller than the remaining amount of the first battery 71*a*, the CPU 48 controls to drive the power supply stop circuit (not shown) to safely stop the system (S106) and ends all the processing.

Referring back to FIG. 31, when the CPU 48 determines in the processing in step S90 that the remaining amount of the first battery 71*a* is larger than the remaining amount of the second battery 71, i.e., the remaining amount of the second battery 71 is smaller than the remaining amount of the first battery 71*a*, as shown in FIG. 34, the CPU 48 controls to supply the driving power by the second battery 71 only to the display device 5 (S107). The CPU 48 controls to supply the driving power by the first battery 71*a* to the flexible endoscope 2 or the rigid endoscope 3 on which the display device 5 is mounted (S108).

Subsequently, the CPU 48 determines whether the remaining charge of the first battery 71*a* is equal to or smaller than the predetermined threshold B (S109). The CPU 48 repeatedly performs processing for returning to step S107 until the remaining charge of the first battery 71*a* decreases to be equal to or smaller than the predetermined threshold B.

When the remaining charge of the first battery 71*a* decreases to be equal to or smaller than the predetermined threshold B, the CPU 48 OSD (on screen display)-displays, on the LCD 42 of the display device 5, a warning to the effect that only a little remaining amount of the first battery 71*a* is left (S110).

Thereafter, the CPU 48 determines whether the remaining charge of the first battery 71*a* is equal to or smaller than the predetermined threshold C (S111). The CPU 48 repeatedly performs processing for returning to step S110 until the remaining charge of the first battery 71*a* decreases to be equal to or smaller than the predetermined threshold C.

When the remaining charge of the second battery 71 decreases to be equal to or smaller than the predetermined threshold C, the CPU 48 controls to drive the power supply stop circuit (not shown) to safely stop the system (S112) and ends all the processing.

After the processing in step S108, the CPU 48 may execute a control example shown in FIG. 35.

Specifically, as shown in FIG. 35, after the processing in step S108, the CPU 48 determines whether the remaining charge of the second battery 71 is equal to or smaller than the predetermined threshold B (S113). The CPU 48 repeatedly performs processing for returning to step S108 until the remaining charge of the second battery 71 decreases to be equal to or smaller than the predetermined threshold B.

When the remaining charge of the second battery 71 decreases to be equal to or smaller than the predetermined threshold B, the CPU 48 OSD (on screen display)-displays, on the LCD 42 of the display device 5, a warning to the effect that only a little remaining amount of the second battery 71 is left (S114).

Thereafter, the CPU 48 determines whether the remaining charge of the second battery 71 is equal to or smaller than the predetermined threshold C (S115). The CPU 48 performs processing for returning to step S114 until the remaining charge of the second battery 71 decreases to be equal to or smaller than the predetermined threshold C.

When the remaining charge of the second battery 71 decreases to be equal to or smaller than the predetermined threshold C, the CPU 48 determines whether the remaining amount of the second battery 71 is smaller than the remaining amount of the first battery 71*a* (S116). When the CPU 48 determines that the remaining amount of the second battery 71 is smaller than the remaining amount of the first battery 71*a*, the CPU 48 stops the control of power supply to the display device 5 by the second battery 71 and switches the driving power by the first battery 71*a* to the display device 5 and all the apparatuses, i.e., the flexible endoscope 2 or the rigid endoscope 3 on which this display device 5 is mounted and controls power supply (S117), However, at this point, the CPU 48 performs control for stopping a part of the functions of the flexible endoscope 2 or the rigid endoscope 3.

Subsequently, the CPU 48 determines whether the remaining charge of the first battery 71*a* is equal to or smaller than the predetermined threshold B (S118). The CPU 48 repeatedly performs processing for returning to step S117 until the remaining charge of the first battery 71*a* decreases to be equal to or smaller than the predetermined threshold B.

When the remaining charge of the first battery 71*a* decreases to be equal to or smaller than the predetermined threshold B, the CPU 48 OSD (on screen display)-displays, on the LCD 42 of the display device 5, a warning to the effect that only a little remaining amount of the first battery 71*a* is left (S119).

Thereafter, the CPU 48 determines whether the remaining charge of the first battery 71*a* is equal to or smaller than the predetermined threshold C (S120). The CPU 48 repeatedly performs processing for returning to step S119 until the remaining charge of the first battery 71*a* decreases to be equal to or smaller than the predetermined threshold C.

When the remaining charge of the first battery 71*a* decreases to be equal to or smaller than the predetermined threshold C, the CPU 48 controls to drive the power supply stop circuit (not shown) to safely stop the system (S121) and ends all the processing.

When the CPU 48 determines in the processing in step S116 that the remaining amount of the second battery 71 is larger than the remaining amount of the first battery 71*a*, i.e., the remaining amount of the first battery 71*a* is smaller than the remaining amount of the second battery 71, the CPU 48 controls to drive the power supply stop circuit (not shown) to safely stop the system (S122) and ends all the processing.

As explained above, it is possible to efficiently control the power supply by the batteries 71 and 71*a* to the display device 5 and the flexible endoscope 2 or the rigid endoscope 3 on which this display device 5 is mounted. When the remaining amounts of the batteries 71 and 71*a* decrease, the LCD 42 of the display device 5 is caused to display a warning to inform the user to that effect. Further, according to the decrease in the remaining amounts of the batteries 71 and 71*a*, the system can be safely stopped.

The second battery for the flexible endoscope and the rigid endoscope 3 may be used as an auxiliary battery. When the second battery is the auxiliary battery in this way, a control example shown in FIG. 36 may be executed.

Specifically, as shown in FIG. 36, first, when the display device 5 is placed on the flexible endoscope 2 or the rigid endoscope 3, the CPU 48 of the display device 5 recognizes a resistance value of the individual identification resistor 64 of the connected apparatus via the connector sections 51 and 52 (S131). The CPU 48 determines whether the first battery 71*a* is mounted on the connected flexible endoscope 2 or rigid endoscope 3 (S132).

When the CPU 48 determines in this processing in step S132 that the first battery 71*a* is mounted on the flexible endoscope 2 or the rigid endoscope 3, the CPU 48 controls to supply, with the first battery 71*a*, power to the flexible endoscope 2 or the rigid endoscope 3 on which this display device 5 is placed (S133). The CPU 48 determines whether the remaining charge of the first battery 71*a* is equal to or smaller than the predetermined threshold B (S134). The CPU 48 repeatedly performs processing for returning to step S133 until the remaining charge of the first battery 71*a* decreases to be equal to or smaller than the predetermined threshold B.

When the remaining charge of the first battery 71*a* decreases to be equal to or smaller than the predetermined threshold B, the CPU 48 OSD (on screen display)-displays, on the LCD 42 of the display device 5, a warning to the effect that only a little remaining amount of the first battery 71*a* is left (S135).

Thereafter, the CPU 48 determines whether the remaining charge of the first battery 71*a* is equal to or smaller than the predetermined threshold C (S136), The CPU 48 repeatedly performs processing for returning to step S135 until the remaining charge of the first battery 71a decreases to be equal to or smaller than the predetermined threshold C.

When the remaining charge of the first battery 71a decreases to be equal to or smaller than the predetermined threshold C, the CPU 48 switches the first battery 71a to the second battery 71 and controls to supply, with this second battery 71, power to the display device 5 and the flexible endoscope 2 or the rigid endoscope 3 on which this display device 5 is mounted (S137).

Subsequently, the CPU 48 determines whether the remaining charge of the second battery 71 is equal to or smaller than the predetermined threshold B (S138). The CPU 48 repeatedly performs processing for returning to step S137 until the remaining charge of the second battery 71 decreases to be equal to or smaller than the predetermined threshold B. When the remaining charge of the second battery 71 decreases to be equal to or smaller than the predetermined threshold B, the CPU 48 OSD (on screen display)-displays, on the LCD 42 of the display device 5, a warning to the effect that only a little remaining amount of the second battery 71 is left (S139).

Thereafter, the CPU 48 determines whether the remaining charge of the second battery 71 is equal to or smaller than the predetermined threshold C (S140). The CPU 48 performs processing for returning to step S139 until the remaining charge of the second battery 71 decreases to be equal to or smaller than the predetermined threshold C. When the remaining charge of the second battery 71 decreases to be equal to or smaller than the predetermined threshold C, the CPU 48 controls to drive the power supply stop circuit (not shown) to safely stop the system (S141) and ends the processing.

When the first battery 71a is not mounted on the flexible endoscope 2 or the rigid endoscope 3 in the processing in step S132, the CPU 48 controls to supply, with the second battery 71, power to the display device 5 and the flexible endoscope 2 or the rigid endoscope 3 on which this display device 5 is placed (S142). The CPU 48 determines whether the remaining charge of the second battery 71 is equal to or smaller than the predetermined threshold B (S143). The CPU 48 repeatedly performs processing for returning to step S142 until the remaining charge of the second battery 71 decreases to be equal to smaller than the predetermined threshold B.

When the remaining charge of the second battery 71 decreases to be equal to smaller than the predetermined threshold B, the CPU 48 OSD (on screen display)-displays, on the LCD 42 of the display device 5, a warning to the effect that only a little remaining amount of the second battery 71 is left (S144).

Thereafter, the CPU 48 determines whether the remaining charge of the second battery 71 is equal to or smaller than the predetermined threshold C (S145). The CPU 48 performs processing for returning to step S144 until the remaining charge of the second battery 71 decreases to be equal to or smaller than the predetermined threshold C.

When the remaining charge of the second battery 71 decreases to be equal to or smaller than the predetermined threshold C, the CPU 48 controls to drive the power supply stop circuit (not shown) to safely stop the system (S146) and ends the processing.

According to such a control example by the CPU 48, when the remaining amount of the first battery 71a decreases, it is possible to perform power supply by the second battery 71, which is the auxiliary battery.

Next, a control example carried out by the CPU 48 of the display device 5 when the display device 5 including the battery 40 is placed on the flexible endoscope 2 or the rigid endoscope 3 including the first battery 71a of the built-in type and when the display device 5 including the battery 40 is placed on the monitor holder 4 as shown in FIG. 25 is explained according to processing shown in flowcharts of FIGS. 37 and 38.

First, when the display device 5 is placed on the monitor holder 4 as shown in FIG. 25, charging of the battery 40 in the display device 5 is started. The monitor holder 4 is in a state in which the AC adapter 74 is connected thereto and the AC adapter 74 is connected to the commercial power supply.

In this state, as shown in FIG. 37, the CPU 48 charges the battery 40 (S151). The CPU 48 determines whether remaining charge of the battery 40 is equal to or larger than the threshold A (S152). The CPU 48 repeatedly performs processing for returning to step S151 until the charging capacity of the battery 40 increases to be equal to or larger than the predetermined threshold A. When the charging capacity of the battery 40 increases to be equal to or larger than the predetermined threshold A in this processing in step S152, the CPU 48 stops the charging to the battery 40 (S153) and ends all the processing.

When the display device 5 is removed from the monitor holder 4 and placed on the flexible endoscope 2 or the rigid endoscope 3, as shown in FIG. 38, the CPU 48 performs charging from the battery 40 to the first battery 71a (S161). The CPU 48 determines whether a charging capacity of the first battery 71a is equal to or larger than the threshold A (S162). The CPU 48 repeatedly performs processing for returning to step S161 until the charging capacity of the first battery 71a increases to be equal to or larger than the predetermined threshold A. When the charging capacity of the first battery 71a increases to be equal to or larger than the predetermined threshold A in this processing in step S162, the CPU 48 stops the charging from the battery 40 to the first battery 71a (S163) and ends all the processing.

In this way, work of the charging may be performed from the battery 40 to the first battery 71a by charging the battery 40 of the display device 5 with the monitor holder 4 connected to the commercial power supply via the AC adapter 74 and, after the battery 40 is charged, placing the display device on the flexible endoscope 2 or the rigid endoscope 3.

Fourth Embodiment

An endoscope system according to a fourth embodiment of the present invention is explained. In the following explanation, components same as those of the endoscope system 1 according to the first embodiment explained above are denoted by the same reference numerals and signs and specific explanation of the components is omitted.

Figure 39:
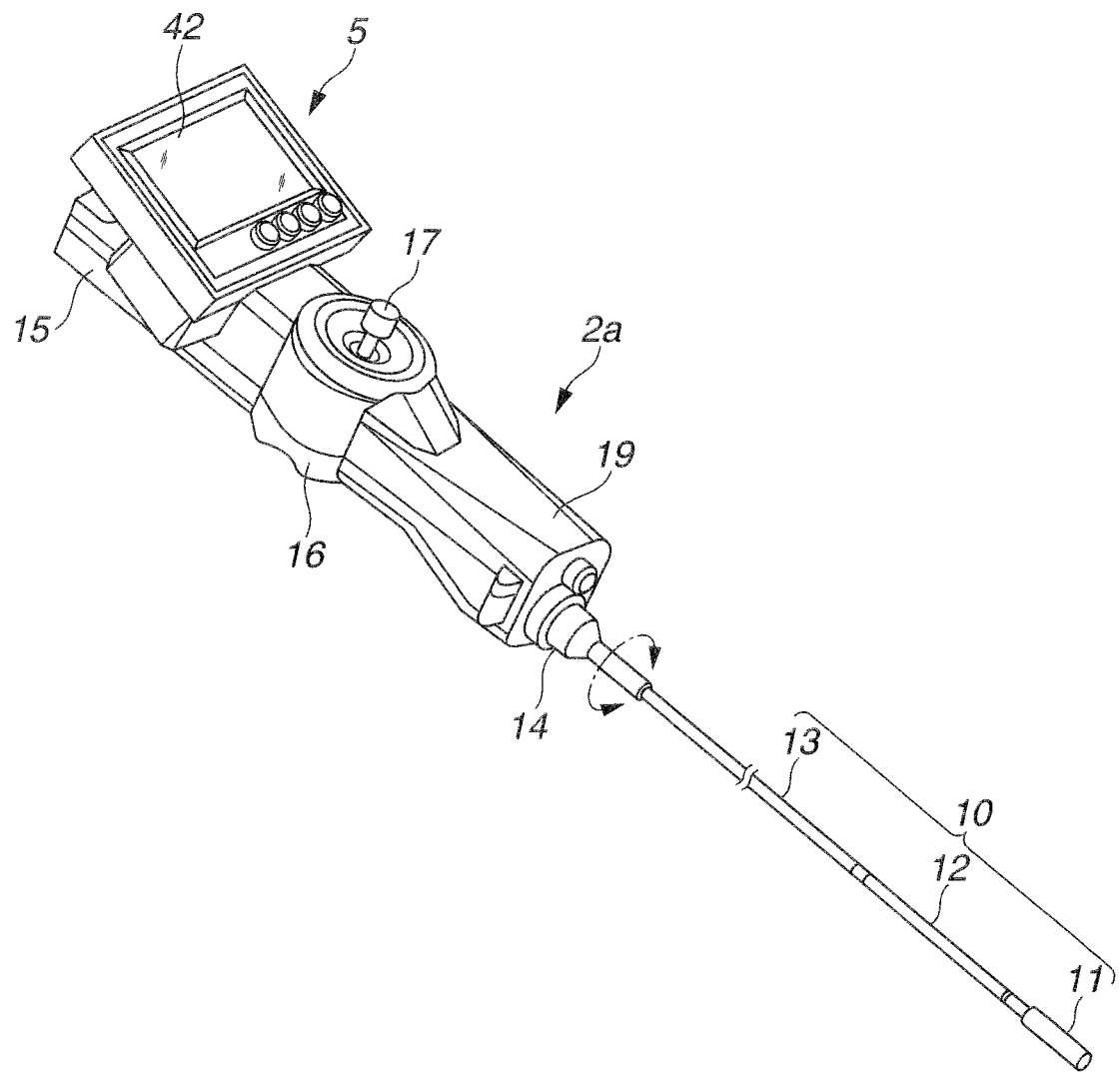
FIG. 39 is a perspective view showing a state in which a display device is placed on a flexible endoscope apparatus according to a fourth embodiment.
Figure 40:
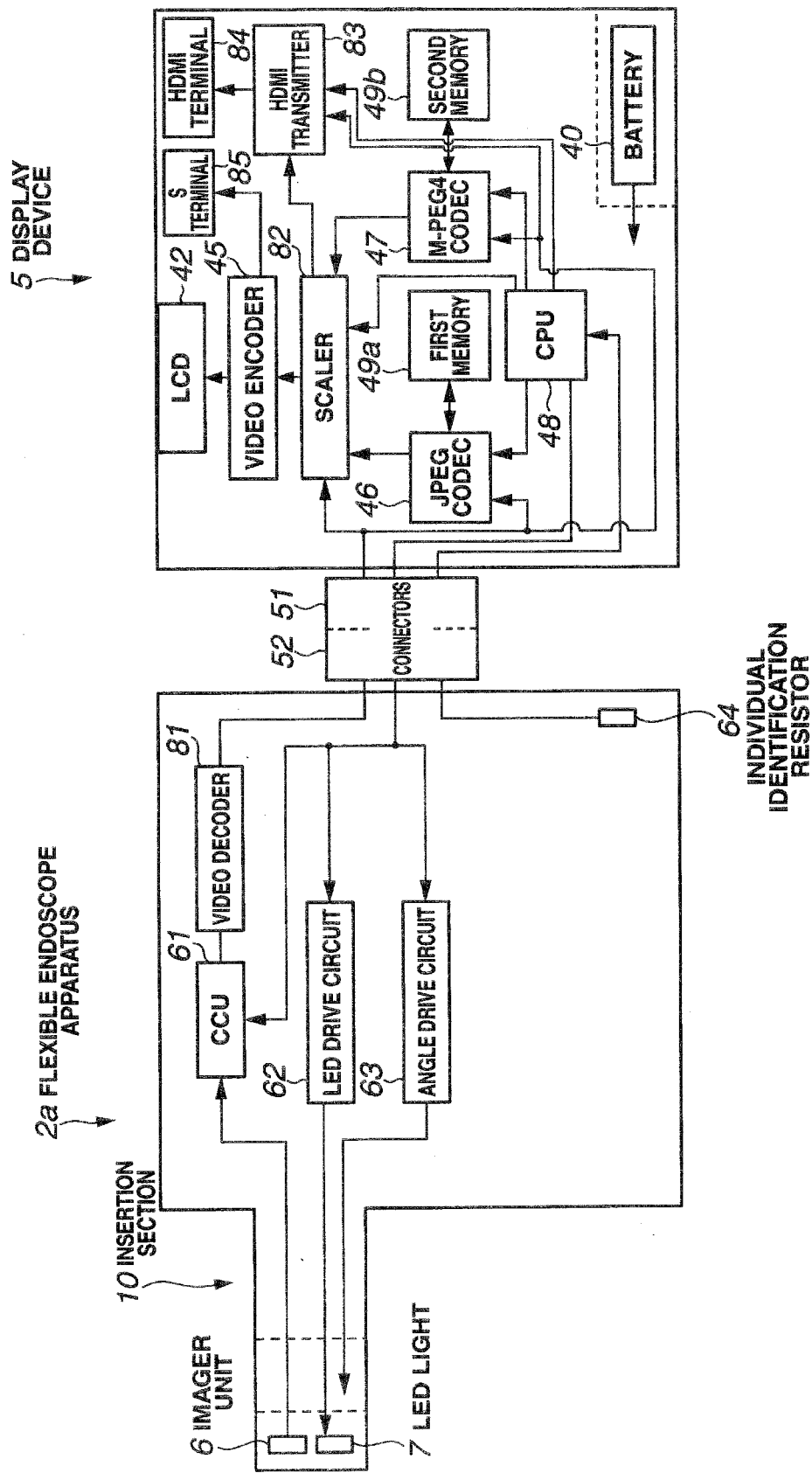
FIG. 40 is a block showing internal configurations of the flexible endoscope apparatus and a monitor holder connected via connector sections according to the fourth embodiment.
Figure 41:
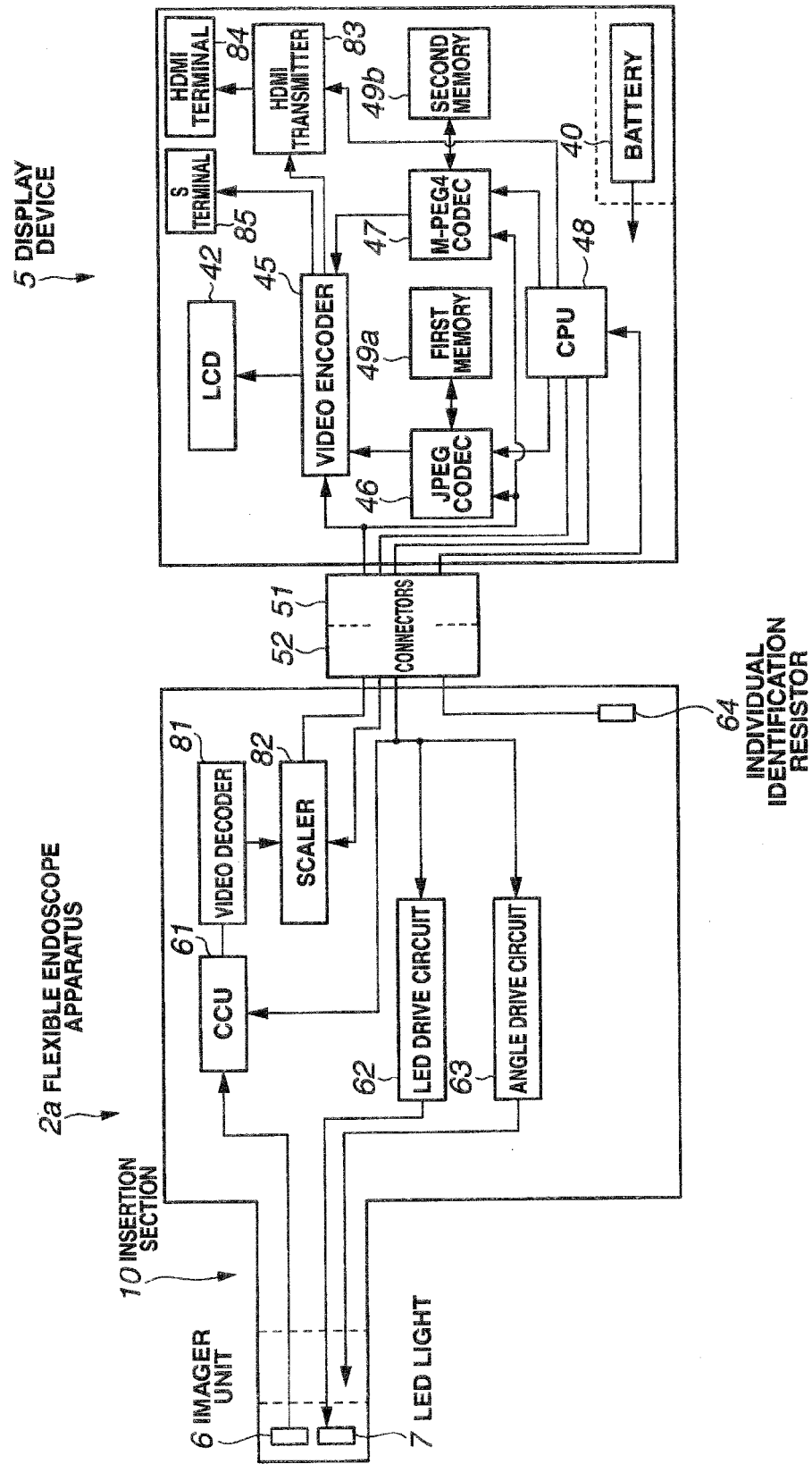
FIG. 41 is a block showing a modification and showing internal configurations of the flexible endoscope apparatus and the monitor holder connected via the connector sections.

FIGS. 39 to 41 relate to the fourth embodiment of the present invention. FIG. 39 is a perspective view showing a state in which a display device is placed on a flexible endoscope apparatus. FIG. 40 is a block showing internal configurations of the flexible endoscope apparatus and a monitor holder connected via connector sections. FIG. 41 is a block showing a modification and showing internal configurations of the flexible endoscope apparatus and the monitor holder connected via the connector sections.

In a flexible endoscope apparatus (hereinafter abbreviated as flexible endoscope in this embodiment as well) 2a in the endoscope system 1 according to this embodiment, in the configuration including the batteries 71 and 71a as shown in FIGS. 22 to 25, a grasping section 19 having a substantially rectangular box shape forming a battery incorporating section for incorporating the batteries 71 and 71a is provided between the insertion section 10 and the bending operation section 16.

In the flexible endoscope 2a according to this embodiment, the flexible tube section 13 of the insertion section 10 is provided continuously from an end face of the grasping section 19 by the bend preventing portion 14 and extends to a user side, i.e., an endoscope operator side. In other words, the flexible endoscope 2a is used in a form in which the insertion section 10 extends to the user side in a state in which the user grasps the grasping section 19 such that the LCD 42 of the display device 5 faces the user.

The insertion section 10 is configured to be pivotable, in a place of the bend preventing portion 14 forming a coupling section with the flexible tube section 13, in a range of about ±90°, i.e., 180° from a predetermined position set as a reference with respect to the grasping section 19. In other words, the flexible tube section 13 is configured to be pivotable longitudinally in a range of 180° with respect to the grasping section 19.

In this way, in the flexible endoscope 2a according to this embodiment, the entire insertion section 10 including the flexible tube section 13 is configured to be pivotable about ±90° with respect to the grasping section 19. Consequently, the user can easily perform observation by the LCD 42. When a grasped state is changed to, for example, a position where the user can easily observe the LCD 42 of the display device 5, the flexible tube section 13 of the insertion section 10 is not twisted. Therefore, a configuration with further improved operability can be obtained. Further, in the flexible endoscope 2, since the flexible tube section 13 extends from the grasping section 19 to the user side during use by the user, it is possible to set a center of gravity position of the entire apparatus near the bending operation section 16. Therefore, the user can grasp the grasping section 19 and use the flexible endoscope 2a in a well-balanced state. Even in endoscope operation for a long time, fatigue during the use by the user is reduced.

First, as shown in FIG. 40, the flexible endoscope 2a according to this embodiment is provided with a video decoder 81 that is connected to the CCU 61 and encodes an input signal in a predetermined manner. In the display device 5 placed on and connected to this flexible endoscope 2a, a scalar 82, which is a data converting section, is interposed between the video encoder 45 and the CPU 48. This scalar 82 is electrically connected to the JPEG codec 46 and the MPEG4 codec 47 as well.

Further, in the display device 5 according to this embodiment, an HDMI transmitter 83 connected to the CPU 48 and the scalar 82, an HDMI terminal 84 functioning as a terminal end of this HDMI transmitter 83, and an S terminal 85 connected to the video encoder 45 are disposed.

In this embodiment, the CPU 61 of the display device 5 recognizes the number of pixels of the imager unit 6 with the individual identification resistor 64 incorporated in the flexible endoscope 2a. The flexible endoscope 2a may include an EEPROM instead of the individual identification resistor 64 and transmit number of pixels information of the imager unit 6 to the CPU 48 of the display device 5 using I2C communication.

Video (image) data outputted from the video decoder 81 of the flexible endoscope 2a is inputted to the scalar 82 of the display device 5. When the CPU 48 recognizes that the number of pixels of the imager unit 6 and the number of pixels of the LCD 42 are different, the CPU 48 instructs the scalar 82 to execute scaling processing to set video data outputted from the video decoder 81 to an image size optimum for the LCD 42. The scalar 82 performs processing to output the video data having the optimum image size to the video encoder 45.

In recording data such as a still image or a moving image outputted from the JPEG codec 46 or the MPEG4 codec 47, when the CPU 48 recognizes that the number of pixels of the imager unit 6 and the number of pixels of the LCD 42 are different, the CPU 48 instructs the scalar 82 to perform the scaling processing such that the recorded data can be displayed in an image size optimum for the LCD 42. The scalar 82 converts the video data on the basis of the instruction and outputs the video data to the video encoder 45.

Specifically, the CPU 48 instructs the scalar 82 to slice the video data and perform processing such as expansion or supplementation according to the image size of the LCD 42 mounted on the display device 5. Conversion processing into the optimum size is performed by the scalar 82. Thereafter, the processed video data is outputted to the video encoder 45. The video encoder 45 outputs the video data to the LCD 42 and causes the LCD 42 to display an image. It goes without saying that, as a size of the imager unit 6, various sizes such as QVGA, CIF, VGA, WVGA, XGA, and HDTV are used.

The HDMI terminal 84 or the S terminal 85 functions as an external video output terminal when the display device 5 is connected to an external monitor to cause the external monitor to display an endoscope image. When the display device 5 is connected to the external monitor via the HDMI terminal 84 or the S terminal 85 in this way, the display device 5 can be set to an image size corresponding to the external monitor according to a command transmitted from the CPU 48 to the scalar 82. In other words, a video to be outputted from the video encoder 45 is selected to be adjusted to a standard of the connected external monitor according to selection by the command of the CPU 48.

As the video data outputted from the video decoder and exchanged between the flexible endoscope 2a and the display device 5, various data such as parallel digital data, serial digital data, LVDS differential serial data, and USB can be used.

As explained above, the various image sizes of the imager unit 6 of the flexible endoscope 2a and the various image sizes of the LCD 42 of the display device 5 can be arbitrarily combined. Consequently, in the configuration according to this embodiment, an optimum image can be acquired in any combination of the apparatuses including selection of the image size and the resolution of the LCD 42 corresponding to an inspection site. Therefore, there is no limitation concerning apparatuses that can be connected. Specifically, since it is not essential to connect the display device 5 and apparatus bodies (the flexible endoscope 2a, etc.) in a one-to-one relation, even if manufacturing and sale of one apparatus body are discontinued, the display device 5 can be attached to the other apparatus and used. Therefore, convenience for a manufacturer and the user is improved. The user can use the inexpensive endoscope system 1.

MODIFICATION

The scalar 82 may be disposed in the flexible endoscope 2a as shown in FIG. 41. In such a configuration, when still image or moving image recording is executed, a function for making it possible to select whether video (image) data processed by the scalar 82 is recorded or video data in an unprocessed state is recorded is provided. As a memory that stores this video data, the video data may be able to be recorded in the third memory 68a and the fourth memory 68b of the flexible endoscope 2a shown in FIG. 18 besides the first memory 49a and the second memory 49b of the display device 5. The other components are the same as the components explained with reference FIG. 40. The same processing by the CPU 48 and the like is executed.

In the embodiments explained above, only the configuration of the flexible endoscope 2a is explained. However, it goes without saying that the components explained above can be applied to the rigid endoscope 3.

The flexible endoscopes 2 and 2a and the rigid endoscope 3 according to the embodiments have the configuration in which the LED lights 7 are arranged in the distal end portions thereof. However, the flexible endoscopes 2 and 2a and the rigid endoscope 3 may have a configuration in which LED light sources are arranged on insides and light guides that transmit illumination light from the LED light sources are provided in the insertion sections 10 and 21.

As explained above, the endoscope system 1 according to the present invention is configured such that the endoscopes 2 and 3 having different functions can be selected as appropriate and the display device 5 can be placed on the endoscopes 2 and 3 in common to be used in various inspections, whereby work efficiency is improved.

What is claimed is:

1. An endoscope system comprising:
   a display device comprising:
      a display;
      a display device-side battery configured to store a charge; and
      a display device-side connector configured to form a first electrical connection with a first apparatus-side connector of a first endoscopic apparatus, wherein the first endoscopic apparatus comprises:
         a first mechanism for performing a first function; and
         a first endoscopic apparatus-side battery for powering the first mechanism to perform the first function; and
   a processor comprising hardware, the processor being configured to:
      control discharging of the display device-side battery through the first electrical connection between the display device-side connector and the first apparatus-side connector of the first endoscopic apparatus to charge the first endoscopic apparatus-side battery;
      determine during charging of the first endoscopic apparatus-side battery whether a charging capacity of the first endoscopic apparatus-side battery is equal to or larger than a first predetermined threshold; and
      stop charging of the first endoscopic apparatus-side battery when the processor determines that the charging capacity of the first endoscopic apparatus-side battery is equal to or larger than the first predetermined threshold.

2. The endoscope system according to claim 1, wherein the display device includes a locking section, and
   a section to be locked configured to engage with the locking section in common is disposed in each of the placing sections.

3. The endoscope system according to claim 2, wherein one of the plural apparatus bodies is an endoscope apparatus having a bending section, and
   the display device is set on the placing section of the endoscope apparatus with an angle, the angle of a monitor screen of the display device and a monitor placing surface in the placing section of the endoscope apparatus being different from an angle of the monitor screen at the time the display device is placed on the placing section of another apparatus of the apparatuses and a monitor placing surface in the placing section of the other apparatus.

4. The endoscope system according to claim 2, wherein, up, down, left, and right directions of the monitor screen of the display device with respect to the plural apparatuses are defined by engagement of the locking section and the section to be locked.

5. The endoscope system according to claim 1, wherein a width dimension of the display device is larger than a width dimension of the placing sections.

6. The endoscope system according to claim 1, further comprising: a first memory disposed in the display device and configured to store image data; and a second memory disposed in each of the plural apparatuses and configured to store the image data.

7. The endoscope system according to claim 1, wherein each of the plural apparatuses includes an individual identification component with which the display device recognizes individual information when the display device is set on the placing section.

8. The endoscope system according to claim 1, further comprising a data converting section disposed in the display device and configured to convert image data into an image size optimum for the monitor screen mounted on the display device and output the image data.

9. The endoscope system according to claim 1, further comprising data converting sections disposed in the plural apparatuses and configured to convert image data into an image size optimum for the monitor screen mounted on the display device and output the image data.

10. The endoscope system according to claim 1,
    wherein the display device-side connector is further configured to form a second electrical connection with a second apparatus-side connector of a second endoscopic apparatus, wherein the second endoscopic apparatus comprises:
       a second mechanism for performing a second function; and
       a second endoscopic apparatus-side battery for powering the second mechanism to perform the second function, and
    wherein the processor is further configured to control discharging of the display device-side battery through the second electrical connection between the display device-side connector and the second apparatus-side connector of the second endoscopic apparatus to charge the second endoscopic apparatus-side battery.

11. The endoscope system according to claim 10, further comprising the first endoscopic apparatus and the second endoscopic apparatus.

12. The endoscopic system according to claim 11,
    wherein the first endoscopic apparatus is one of a flexible endoscope and a rigid endoscope, and
    wherein the second endoscopic apparatus is the other of the flexible endoscope and the rigid endoscope.

13. The endoscope system according to claim 1,
    wherein the display device-side connector is further configured to form a charging electrical connection with a holder-side connector of a holder, wherein the holder comprises an adapter connected to a power supply, and
    wherein the processor is further configured to control charging of the display device-side battery by the power supply through the charging electrical connection between the display device-side connector and the holder-side connector.

14. The endoscopic system according to claim 13, the processor is further configured to:
    determine during the charging of the display device-side battery whether a charging capacity of the display device-side battery is equal to or larger than a second predetermined threshold; and stop the charging of the display device-side battery when the processor determines that the charging capacity of the display device-side battery is equal to or larger than the second threshold.

* * * * *